(12) United States Patent
Ngai

(10) Patent No.: US 9,029,277 B2
(45) Date of Patent: May 12, 2015

(54) BREATHABLE LAMINATE AND METHOD OF MAKING SAME

(75) Inventor: Mou Chung Ngai, Boxmeer (NL)

(73) Assignee: Polymer Group, Inc., Charlotte, NC (US)

( * ) Notice: Subject to any disclaimer, the term of this patent is extended or adjusted under 35 U.S.C. 154(b) by 445 days.

(21) Appl. No.: 13/094,868

(22) Filed: Apr. 27, 2011

(65) Prior Publication Data

US 2012/0034837 A1    Feb. 9, 2012

(30) Foreign Application Priority Data

Aug. 4, 2010  (EP) ................................... 10008148

(51) Int. Cl.
| | |
|---|---|
| B32B 27/12 | (2006.01) |
| B29C 71/00 | (2006.01) |
| A61F 13/514 | (2006.01) |
| B32B 5/02 | (2006.01) |
| B32B 27/30 | (2006.01) |
| B29C 47/00 | (2006.01) |
| B32B 3/26 | (2006.01) |
| B32B 5/24 | (2006.01) |
| B32B 5/22 | (2006.01) |
| B32B 27/32 | (2006.01) |
| B32B 27/36 | (2006.01) |

(52) U.S. Cl.
CPC ......... *A61F 13/5148* (2013.01); *B29C 47/0021* (2013.01); *B32B 3/263* (2013.01); *B32B 5/24* (2013.01); *B32B 5/22* (2013.01); *A61F 13/51458* (2013.01); *B32B 27/12* (2013.01); *B32B 5/022* (2013.01); *B32B 27/302* (2013.01); *B32B 27/306* (2013.01); *B32B 27/32* (2013.01); *B32B 27/36* (2013.01); *B32B 2307/724* (2013.01); *B32B 2419/00* (2013.01); *B32B 2439/00* (2013.01); *B32B 2535/00* (2013.01); *B32B 2555/02* (2013.01); *B32B 2309/14* (2013.01)

(58) Field of Classification Search
None
See application file for complete search history.

(56) References Cited

U.S. PATENT DOCUMENTS

| | | | |
|---|---|---|---|
| 4,342,314 | A | 8/1982 | Radel et al. |
| 4,347,844 | A | 9/1982 | Ohki et al. |

(Continued)

FOREIGN PATENT DOCUMENTS

| | | | |
|---|---|---|---|
| EP | 0893530 | * | 1/1999 |
| EP | 0893530 A1 | | 1/1999 |

(Continued)

OTHER PUBLICATIONS

Typar Landscapes http://www.typarlandscape.com/IS_uses.html.*

(Continued)

*Primary Examiner* — Angela Ortiz
*Assistant Examiner* — Shawnda McKinnon
(74) *Attorney, Agent, or Firm* — Kilyk & Bowersox, P.L.L.C.; Todd M. Hess

(57) ABSTRACT

A breathable laminate has a liquid-resistant backing film layer having varied vapor permeability that includes breathable thinned localized regions and thicker non-breathable regions, wherein the film layer is co-extensively directly joined with a liquid- and vapor-permeable nonwoven fabric. The breathable laminate can have unidirectional air permeability. The present invention also relates to disposable apparel and absorbent products which incorporate the breathable laminate, and methods of making the breathable laminate.

20 Claims, 8 Drawing Sheets

(56) References Cited

U.S. PATENT DOCUMENTS

| | | | |
|---|---|---|---|
| 4,797,171 | A | 1/1989 | Van Gompel |
| 5,628,097 | A | 5/1997 | Benson et al. |
| 5,865,926 | A | 2/1999 | Wu et al. |
| 5,916,661 | A | 6/1999 | Benson et al. |
| 6,042,575 | A | 3/2000 | Osborn, III et al. |
| 6,087,551 | A * | 7/2000 | Pereira ................. 604/367 |
| 6,132,410 | A | 10/2000 | Van Gompel et al. |
| 6,140,551 | A | 10/2000 | Niemeyer et al. |
| 6,142,983 | A | 11/2000 | Suprise et al. |
| 6,152,904 | A | 11/2000 | Matthews et al. |
| 6,177,607 | B1 | 1/2001 | Blaney et al. |
| 6,217,890 | B1 | 4/2001 | Paul et al. |
| 6,218,593 | B1 | 4/2001 | Torimae et al. |
| 6,221,460 | B1 | 4/2001 | Weber et al. |
| 6,224,961 | B1 | 5/2001 | Hsueh et al. |
| H001969 | H | 6/2001 | Fell et al. |
| 6,264,642 | B1 | 7/2001 | Kuen et al. |
| H001978 | H | 8/2001 | Freiburger et al. |
| 6,296,862 | B1 | 10/2001 | Paul et al. |
| 6,316,013 | B1 | 11/2001 | Paul et al. |
| H0002011 | H * | 1/2002 | Freiburger et al. |
| H002011 | H | 1/2002 | Freiburger et al. |
| 6,410,465 | B1 | 6/2002 | Lim et al. |
| 6,414,217 | B1 | 7/2002 | Uitenbroek et al. |
| 6,440,111 | B1 | 8/2002 | Berba et al. |
| 6,452,062 | B1 * | 9/2002 | Koczab ................. 604/383 |
| 6,455,753 | B1 | 9/2002 | Glaug et al. |
| 6,458,110 | B1 | 10/2002 | Lavon et al. |
| 6,459,016 | B1 | 10/2002 | Rosenfeld et al. |
| 6,465,712 | B1 | 10/2002 | Matthews et al. |
| 6,482,422 | B1 | 11/2002 | Paul et al. |
| 6,486,379 | B1 | 11/2002 | Chen et al. |
| 6,491,677 | B1 | 12/2002 | Glaug et al. |
| 6,491,928 | B1 | 12/2002 | Smith, III |
| 6,492,574 | B1 | 12/2002 | Chen et al. |
| 6,503,236 | B1 | 1/2003 | Uitenbroek et al. |
| 6,503,525 | B1 | 1/2003 | Paul et al. |
| 6,503,526 | B1 | 1/2003 | Krzysik et al. |
| 6,506,695 | B2 * | 1/2003 | Gardner et al. ................. 442/76 |
| 6,509,513 | B2 | 1/2003 | Glaug et al. |
| 6,521,813 | B1 | 2/2003 | Chihani |
| 6,552,245 | B1 | 4/2003 | Roessler et al. |
| 6,569,139 | B1 | 5/2003 | Datta et al. |
| 6,573,422 | B1 | 6/2003 | Rosenfeld et al. |
| 6,583,331 | B1 | 6/2003 | McCormack et al. |
| 6,585,713 | B1 | 7/2003 | LeMahieu et al. |
| 6,586,653 | B2 | 7/2003 | Graeme, III et al. |
| 6,590,136 | B1 | 7/2003 | Young et al. |
| 6,592,561 | B2 | 7/2003 | Simard et al. |
| 6,595,042 | B2 | 7/2003 | Holliday et al. |
| 6,595,977 | B1 | 7/2003 | Luizzi, Jr. et al. |
| 6,608,237 | B1 | 8/2003 | Li et al. |
| 6,663,611 | B2 | 12/2003 | Blaney et al. |
| 6,673,418 | B1 | 1/2004 | DeOlivera et al. |
| 6,689,242 | B2 | 2/2004 | Bodaghi |
| 6,781,027 | B2 | 8/2004 | Fenwick et al. |
| 6,803,496 | B2 | 10/2004 | Elder et al. |
| 6,808,790 | B2 | 10/2004 | Chen et al. |
| 6,851,593 | B2 | 2/2005 | Weber et al. |
| 6,932,802 | B2 | 8/2005 | Luizzi et al. |
| 6,946,585 | B2 | 9/2005 | London Brown |
| 6,972,011 | B2 | 12/2005 | Maeda et al. |
| 7,003,804 | B2 * | 2/2006 | Lewis ................. 2/51 |
| 7,081,560 | B1 | 7/2006 | Lim et al. |
| 7,138,561 | B2 * | 11/2006 | Fuchs et al. ................. 604/378 |
| 7,148,160 | B2 | 12/2006 | Porter |
| 7,166,094 | B2 | 1/2007 | Glaug et al. |
| 7,226,880 | B2 | 6/2007 | Potnis |
| RE39,919 | E | 11/2007 | Dodge, II et al. |
| 7,294,218 | B2 | 11/2007 | Haque et al. |
| 7,314,840 | B2 | 1/2008 | Baychar |
| 7,396,782 | B2 | 7/2008 | Blenke et al. |
| 7,438,707 | B2 | 10/2008 | Bushman et al. |
| 7,452,834 | B2 | 11/2008 | Nagahara |
| 7,473,817 | B1 | 1/2009 | Tanaka et al. |
| 7,488,310 | B2 | 2/2009 | Yang |
| 7,514,071 | B2 | 4/2009 | Simon et al. |
| 7,549,981 | B2 | 6/2009 | Tanio et al. |
| 7,553,783 | B2 | 6/2009 | Tanaka |
| 7,594,905 | B2 | 9/2009 | Tanio et al. |
| 7,597,689 | B2 | 10/2009 | Hoffmann et al. |
| 2010/0255270 | A1 * | 10/2010 | Stuebiger ................. 428/201 |

FOREIGN PATENT DOCUMENTS

| | | | |
|---|---|---|---|
| EP | 0955158 A2 | | 11/1999 |
| EP | 1543952 | * | 6/2005 |
| EP | 1543952 A2 | | 6/2005 |
| EP | 1232059 B1 | | 10/2006 |
| WO | 9745259 A1 | | 12/1997 |
| WO | WO9745259 | * | 12/1997 |

OTHER PUBLICATIONS

Machine translation of KR2007047492, May 2007, Choi et al.*

Extended European Search Report for priority application No. EP10008148.8-2124, Feb. 24, 2011, 4 pages total.

* cited by examiner

FIG. 11
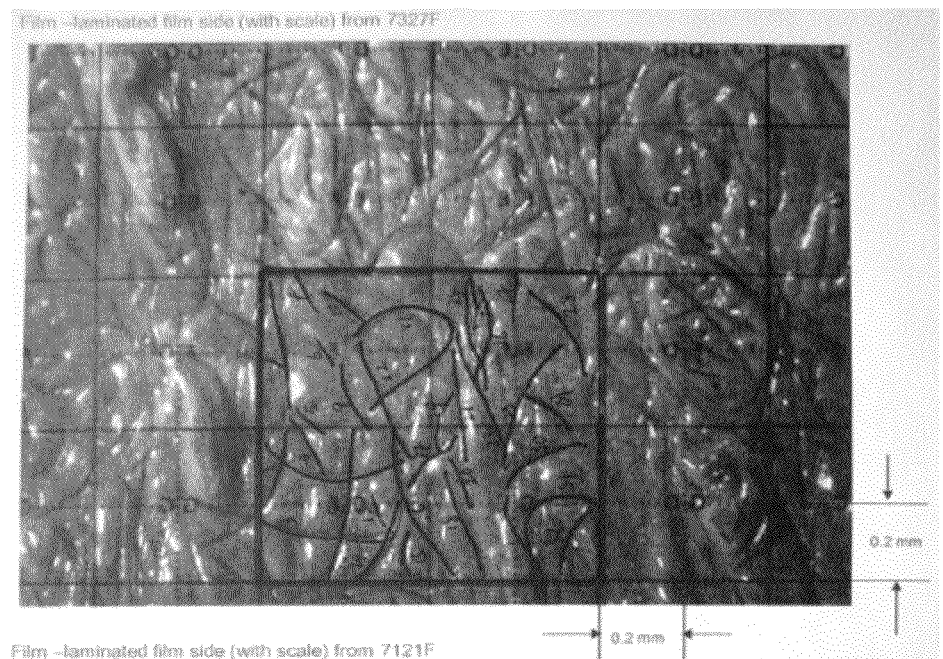
FIG. 12

Table 3   FIG. 14

| | Light Green (7121) | Dark Green (7327) | Light Green (7121) | Dark Green (7327) |
|---|---|---|---|---|
| | Before Calender | | After Calendering P130 (40 bars - Cold) | |
| | NWF/FILM / FILM | FILM / FILM | FILM / FILM | FILM / FILM |

| | Light Green (7121) | | Dark Green (7327) | | Light Green (7121) | | Dark Green (7327) | |
|---|---|---|---|---|---|---|---|---|
| Air Porosity (l/m²/s) (20cm²; 196Pa) ENISO 9237:1995 | 2.53 | 0 | 2.42 | 0 | 1.12 | 0 | 1.25 | 0 |
| | 2.16 | 0 | 2.75 | 0 | 1.15 | 0 | 0.95 | 0 |
| | 2.67 | 0 | 2.76 | 0 | 0.95 | 0 | 1.16 | 0 |
| | 2.58 | 0 | 2.79 | 0 | 1.14 | 0 | 0.98 | 0 |
| | 2.43 | 0 | 2.65 | 0 | 0.9 | 0 | 1.24 | 0 |
| | 2.14 | 0 | 2.5 | 0 | 1.1 | 0 | 1 | 0 |
| Average | 2.42 | 0.00 | 2.66 | 0.00 | 1.06 | 0.00 | 1.10 | 0.00 |

| | Light Green (7121) | | Dark Green (7327) | | Light Green (7121) | | Dark Green (7327) | |
|---|---|---|---|---|---|---|---|---|
| HSH at 10mbar/min EN1174-2:1992 | 39 | 12 | 79 | 27 | 33 | 8 | 68 | 17 |
| | 44 | 16 | 88 | 35 | 39 | 12 | 66 | 15 |
| | 45 | 15 | 93 | 28 | 35 | 11 | 73 | 17 |
| | 46 | 18 | 78 | 26 | 32 | 9 | 73 | 14 |
| | 50 | 16 | 85 | 28 | 33 | 10 | 69 | 14 |
| | 48 | 15 | 84 | 33 | 36 | 9 | 71 | 13 |
| average | 45 | 15 | 85 | 30 | 35 | 10 | 70 | 15 |

| | Light Green (7121) | | Dark Green (7327) | |
|---|---|---|---|---|
| Water Vapor Transmission ASTM 96 (32°C 50% RH): g/m²·d | 13.68 | 13.44 | 14.88 | 15.12 |
| | 14.4 | 13.44 | 15.6 | 13.68 |
| | 16.08 | 13.44 | 16.08 | 12.24 |
| | 14.7 | 13.4 | 15.6 | 13.7 |

| | Light Green (7121) | Dark Green (7327) |
|---|---|---|
| Water Vapor Transmission ISO 15106-3 23°C/In Contact with Water: g/m²·d | 19 | 9.75 |
| | 14 | 10.6 |
| | 16.5 | 10.2 |

| | Light Green (7121) | | Dark Green (7327) | | Light Green (7121) | | Dark Green (7327) | |
|---|---|---|---|---|---|---|---|---|
| Burst Strength (Kpa) EN 13938-1:1999 | 301 | 290 | 290 | 275 | 290 | 287 | 250 | 254 |
| | 283 | 282 | 277 | 260 | 293 | 296 | 250 | 254 |

| Barrier Index (BI) ISO 22610:2006 | Light Green (7121) | Dark Green (7327) |
|---|---|---|
| | Film side - outside of gown | |
| | 6 | 6 |

BREATHABLE LAMINATE AND METHOD OF MAKING SAME

This application claims priority from European Patent Application No. 10008148.8, filed Aug. 4, 2010.

FIELD OF THE INVENTION

The present invention relates to a breathable laminate comprising a liquid-resistant backing film layer having varied vapor permeability including breathable thinned regions and thicker non-breathable regions, wherein the film layer is in co-extensive, directly-joined contact with a nonwoven fabric. The present invention also relates to disposable apparel and absorbent products which incorporate the breathable laminate, and methods of making the breathable laminate.

BACKGROUND OF THE INVENTION

There is an increasing need for better protection via barriers to liquids, bacteria, or viruses, without sacrificing comfort, e.g., breathability and absorbency, for disposable personal protective apparel and disposable absorbent articles.

Vapor or gas permeable, microporous "breathable" material that is permeable to vapors or gas yet substantially impermeable to liquid have been developed in the past. Breathability previously has been imparted in polymer films by using inorganic fillers in the film polymer formulation, extruding the filler/polymer formulation into a film, and then mechanically stretching the film sufficiently to create voids around the filler particles, to make the film breathable. In a subsequent separate process, the breathable film made with inorganic filler in such a manner can be laminated with a nonwoven web using adhesive or a point-bonding calendar to produce a soft, textile like composite. Monolithic membranes or films also have been previously developed that of polymer resins that allow the passage of water vapor because of the hydrophilic character of the resin itself. These previous monolithic membranes/films are "breathable" barriers in the sense that the film acts as a barrier to liquids, but have passages with cross-sectional sizes on a molecular scale formed by a polymerization process. The passages serve as conduits by which water (or other liquid) vapor molecules can pass through the film as a result of a concentration gradient across the monolithic membrane or film. This process is referred to as activated diffusion. However, raw materials for such monolithic "breathable" films are relatively expensive when compared to conventionally used polyolefins such as polyethylene and polypropylene and their copolymers. Solutions for imparting breathability in films that do not require specialty chemicals, and instead can use more economical and widely available raw materials are needed.

U.S. Pat. No. 6,087,551 relates to a multi-denier non-woven fabric suitable for use as a body side liner in disposable absorbent products having an absorbent core positioned between a non-woven fabric and a separately preformed, body fluid-impermeable backing sheet. The multi-denier non-woven fabric is made from an interconnected network thermoplastic polymer fibre elements comprising a homogeneous blend of high denier and low denier fibres.

U.S. Pat. No. 6,781,027, similar to U.S. Pat. No. 6,087,551, relates in part to a composite structure including a mixed denier nonwoven fabric made of a homogeneous blend of large and small denier fibres. U.S. Pat. No. 6,781,027, similar to similar to U.S. Pat. No. 6,087,551 as well as U.S. Pat. Nos. 6,595,042 and 6,946,585, shows a nonwoven fabric combined with a fluid impermeable backing sheet in a structure including an intervening absorbent core. The nonwoven fabric and backing sheet in these references appear to be combined as separately preformed layers.

SUMMARY OF THE PRESENT INVENTION

The present invention is directed to a breathable laminate comprising a liquid-resistant backing film layer having varied vapor permeability in co-extensive direct joined contact with a liquid- and vapor-permeable nonwoven fabric. The backing film layer of the breathable laminate comprises thinned localized regions which are vapor-permeable and liquid-resistant and thicker regions which are vapor-impermeable and liquid-resistant. The backing film layer comprises a thermoplastic resin-containing composition; and it is co-extensively directly joined to a nonwoven fabric comprising a blend of first decitex fibres and second decitex fibres which differ by at least 1 decitex, wherein the first decitex fibres have a decitex in a range of from 3.5 to 15 and the second decitex fibres have a decitex in a range of from 0.5 to 3.5. The first decitex fibres are present in the blend in an amount of from 10% to 90% by weight and the second decitex fibres are present in the blend in an amount of from 90% to 10% by weight.

In one embodiment, the present invention is directed to a breathable laminate comprising a nonwoven fabric and film composite constructed with a normally non-breathable polymeric resin that is extruded onto the surface of the above-indicated mixed decitex fibre blend nonwoven fabric and cooled to form a polymeric film thereon. Thinner film areas/zones of the polymeric film are formed on the first decitex fibres of the fibre blend and thicker film area/zones are formed on the second decitex fibres of the fibre blend included in the nonwoven fabric. Unidirectional air permeability can be formed in the breathable laminate composite structure.

In another embodiment, the breathable laminate can form part of a disposable garment, such as a disposable medical gown. The breathable laminates including these features also can be used, for example, in other disposable products, such as surgical drapes, diapers, sanitary napkins, panty liners, underpads, wound care articles, wipes, or other medical, personal care, construction, or industrial products where combined absorbency, vapor permeability, and leak barrier properties in a unitary drapeable sheet-like product are useful.

In another embodiment, a method of making a breathable laminate with varied vapor permeability is provided by extrusion lamination (coating) of a film-forming polymeric resin directly onto a nonwoven fabric to form an extrusion coated nonwoven fabric, where the nonwoven fabric comprises first and second decitex fibres which differ by at least 1 decitex. The extrusion lamination can be performed at the nip region of pressure rolls to form an extrusion coated nonwoven fabric. The extrusion coated nonwoven fabric is cooled to produce a liquid resistant and varied vapor-permeability backing film layer co-extensively in direct joined contact with a liquid- and vapor-permeable nonwoven fabric. The blend of mixed decitex fibres in the nonwoven fabric can interact with the extruded polymeric film to form vapor-permeable, liquid-resistant localized thinned regions in the extruded backing film layer that remain after cooling the coated nonwoven fabric sufficient to harden the extruded polymeric resin into a varied vapor permeability film attached to the nonwoven fabric. The first decitex fibres also can be different in chemical composition from the second decitex fibres to further enhance the varied breathability imparted to the film.

It is to be understood that both the foregoing general description and the following detailed description are exemplary and explanatory only and are intended to provide a further explanation of the present invention, as claimed.

The accompanying drawings, which are incorporated in and constitute a part of this application, illustrate some of the embodiments of the present invention and together with the description, serve to explain the principles of the present invention.

BRIEF DESCRIPTION OF DRAWINGS

FIG. 11 is a microphotograph (200×) from the laminated film side, with scale and thread markings, of a film of a comparison laminate.

FIG. 12 is a microphotograph (200×) from the laminated film side, with scale and thread markings, of a film of a breathable laminate in accordance with an embodiment of the present invention.

FIG. 14 illustrates Table 3 as referred to herein.

DEFINITIONS

Figure 1:
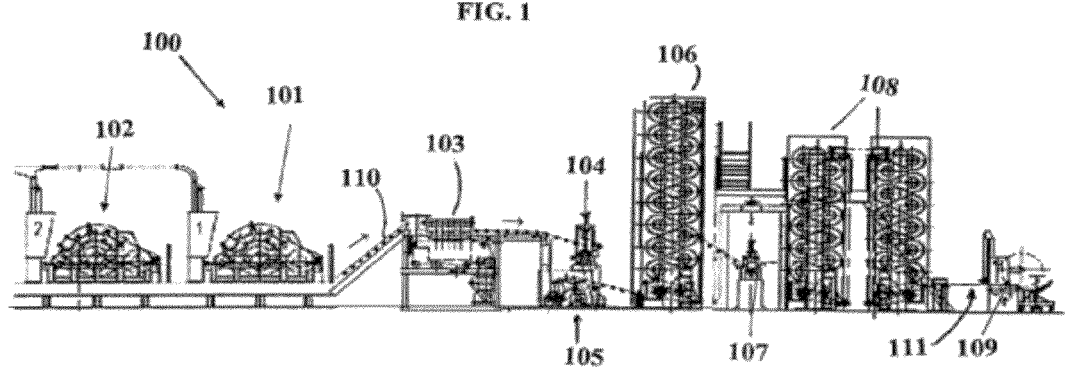
FIG. 1 is a schematic view of an equipment arrangement for making a nonwoven fabric of a breathable laminate in accordance with an embodiment of the present invention.

As used herein, the term "breathable laminate" refers to a laminate material comprising a nonwoven fabric attached to a film layer, wherein the laminate has a water vapor transmission rate ("WVTR") of at least 8 grams/$m^2$/24 hours (with vapor pressure applied from the nonwoven fabric side), using WVTR Test Procedures in accordance with ISO 15106-3 (testing in direct contact with water), which testing procedures are described in the examples section herein. The water vapor transmission rate test, generally speaking, measures the mass or volume of vapor transported across the cross section of the film in a given unit of time at a defined set of environmental conditions. The film and nonwoven fabric components of a laminate may have different breathability. Nonetheless, if the laminate exhibits breathability, then it follows that each of the film and nonwoven components of the laminate is each breathable at least to the prescribed level. In view of practical challenges to directly measuring breathability of an extruded film alone that has been delaminated from the nonwoven fabric of a laminate, breathability for purposes herein is measured on a laminate basis including the film.

As used herein, "vapor-permeable" refers to a breathable laminate or film. As indicated, if the laminate exhibits breathability, then it follows that each of the film and non-woven components of the laminate is each breathable at least to the prescribed level. A "vapor-impermeable" laminate or film does not meet the stated definition of "vapor-permeable".

As used herein, "liquid-resistant laminate" refers to a laminate comprising a nonwoven fabric attached to a film layer, wherein the laminate has a hydrostatic head value of at least 5 or more as measured at 10 mbar/min (for both conditions of water pressure applied from either the fabric side or the film side), using the Hydrostatic Head (HSH) Value Test Procedure described in the examples section herein. Higher HSH values are indicative of greater liquid barrier property. Where the laminate is used in a product as a body liner, for example, the HSH measurement with water pressure applied from the fabric side can provide a measure of the laminate's resistance to leakage of liquids taken up by the nonwoven fabric. A HSH measurement with water pressure applied from the film side can provide a measure of the laminate's resistance to penetration of liquids, such as bodily fluids and liquid chemicals, into the laminate from the film side. As can be appreciated, pressure conditions associated with the testing used may induce some liquid throughput that would not be associated with the material in normal uses. Accordingly, a "liquid-resistant" laminate referred to herein is substantially liquid-impermeable or entirely liquid-impermeable based on the indicated HSH test protocols. A "liquid-permeable" laminate does not meet the stated definition of "liquid-resistant".

As used herein, a "liquid-resistant film" or "liquid-resistant backing film" refers to a film that inhibits the penetration of liquids into a laminate comprising a nonwoven fabric attached to the film layer from at least one of the film side, fabric side, or both, as compared to the nonwoven fabric alone. For example, a laminate comprising a liquid-resistant film or liquid resistant backing film can have a hydrostatic head value of at least 5% greater as compared to the non-woven fabric alone, as measured at 10 mbar/min (for both conditions of water pressure applied from either the film side or the fabric side), using the Hydrostatic Head (HSH) Value Test Procedure described in the examples section herein.

As used herein, "thinned localized region" or "thinned localized regions" refers to a region or regions of the backing film layer which is (are) vapor-permeable and liquid-resistant. The thinned localized regions are essentially entirely composed (e.g., >98 vol %) of solid film composition material instead of air space. The thinned localized regions therefore are essentially solid film construction and are not film through-holes, air passages, or entrapped gas bubbles.

As used herein, "thicker region" or "thicker regions" refers to a region or regions of the backing film layer which is (are) vapor-impermeable and liquid-resistant. The thicker regions are essentially entirely composed (e.g., >99 vol %) of solid film composition material instead of air space. For purposes herein, the thickness parameter of the film layer is oriented normal to the opposite major faces or sides of the film. The thinner and thicker regions can be substantially or completely contiguous with each other, i.e., these regions can directly merge and border each other as part of a continuous film.

As used herein, "nonporous" refers to the absence of through-holes and air passages extending continuously between opposite sides (i.e., major surfaces) of a film. As used herein, "through-holes" are holes made by physical processing for breathability or other reasons that extend through the entire thickness of the film with openings at each side of the film which are connected by a continuous air passage.

As used herein, "hydrophobic" refers to a film or other material that contains chemical structures, such as functional groups and/or polymeric chain structures, that repel water.

The term "polymer" or "polymeric" includes, but is not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to isotactic, syndiotactic and atactic symmetries.

As used herein, the term "fibre" generally can refer to continuous filaments, substantially continuous filaments, and staple fibres, and other fibrous structures having a length that is substantially greater than its diameter, unless indicated otherwise.

As used herein, "decitex" is defined as grams per 10,000 meters of a fibre. A lower decitex indicates a finer fibre and a higher decitex indicates a thicker or coarser fibre. As a practical matter, a bale or other source(s) of a given type of fibre may not be precisely a single decitex throughout, as some minor variation may be present. As used herein, at least 80% up to 100% of a given first fibre (or given second fibre, as applicable) have an absolute decitex value within ±7% of the stated decitex value. For example, first fibres stated herein to have a decitex of 15, means 80-100% of the first fibres have a decitex in the range of 14 to 16.

For a fibre having circular cross-section, decitex may be calculated in an approximate manner as known fibre diameter for the fibre, such as by fibre diameter in microns squared, multiplied by the density in grams/cc, multiplied by 0.00786. For example, a diameter of a polypropylene (PP) fibre given as 25 microns (μm) may be converted to decitex by squaring 25, multiplying the result by 0.89 g/cc (the PP fibre density), and multiplying by ($1/100 \cdot \pi/4$) or 0.00785. Thus, a 25 micron polypropylene fibre has a decitex of about 4.4 ($25^2 \times 0.89 \times 0.00785 = 4.4$). In the United States, the unit of measurement is more commonly the denier, which is defined as the grams per 9000 meters of fibre. Decitex may be calculated from a denier value as: denier×10/9.

As used herein, a "nonwoven" or "nonwoven web" refers to a fibre-containing material which is formed without the aid of a textile weaving or knitting process.

As used herein, a "layer" is defined as a generally recognizable combination of similar material types or function existing in the X-Y plane.

As used herein, a "laminate" refers to two or more layers joined together to have a substantial portion of their common X-Y plane interfacing.

As used herein, "comprising" or "comprises" is synonymous with "including," "containing," "having", or "characterized by," and is open-ended and does not exclude additional, unrecited elements or method steps, and thus should be interpreted to mean "including, but not limited to . . . ".

As used herein, "consisting of" excludes any element, step, or ingredient not specified.

As used herein, "consisting essentially of", refers to the specified materials or steps and those that do not materially affect the basic and novel characteristic(s) of the breathable laminates of the invention as further described herein.

DETAILED DESCRIPTION OF THE PRESENT INVENTION

The present invention relates to a breathable laminate having a nonwoven fabric and a liquid-resistant backing film layer having varied vapor permeability directly attached together in a co-extensive configuration. The nonwoven fabric component of the laminate contains a blend of fibres having different fibre sizes such that coarser fibres of the fibre blend can impart breathable thinned localized regions in the backing film layer during manufacture of the laminate. Accordingly, the backing film layer can be formed of a polymeric composition that normally would be non-breathable if extruded onto the surface of a nonwoven fabric formed by fibres only of the same fibre diameter, same chemical nature, same adhesion character to the polymer film, and same physical properties—especially the fibre resiliency property. The breathable thinned localized regions formed in the backing film layer of the breathable laminate can be surrounded at least in part by thicker non-breathable film regions of the film layer. The thinned localized regions and thicker regions in the film layer form a leak barrier to liquids, but the thinned localized regions (but not the thicker regions) can selectively allow passage of vapors (e.g., moisture vapors) through the backing film layer. The resulting backing film layer can be a combination of thinned breathable film regions (such as spots, lines, and other discrete regions), and thicker non-breathable adjoining and surrounding film regions. For example, liquids, such as body liquids, absorbed by the nonwoven fabric can hardly pass through any region of the backing film layer, but vapors can pass through the thinned regions (e.g., moisture vapor, ammonia gas, etc.). The backing film layer imparted with the thinned localized regions also can be effective to exclude passage of microorganisms (e.g., bacteria, viruses) through the backing film layer, while permitting water or gas vapors to pass through the film layer.

The present invention also relates to breathable laminates which comprise a nonwoven fabric and film composite constructed using a normally non-breathable polymeric resin which is extruded onto the surface of the nonwoven fabric having as above-indicated a mixed decitex fibre blend and cooled to form a polymeric film thereon, wherein thinner film areas/zones of the polymeric film are formed on the coarser fibres (i.e., first decitex fibres) of the fibre blend and thicker film area/zones are formed on the finer fibres (i.e., second decitex fibres) of the fibre blend. Unidirectional air permeability can be formed in the laminated composite structure.

As the breathable film component of the laminate of the present invention can provide a barrier to liquid transfer and/or microbial transfer, but permits passage of vapors, air, or both, there are a variety of applications, many of which are in direct or indirect contact with skin, which can take advantage of this unique combination of properties. For example, when in close proximity to the skin, the breathable laminate can allow the body to cool itself naturally, e.g., excess moisture to evaporate, and/or allow vapors from bodily liquids, such as ammonia, to be released. The breathable laminate also controllably absorbs body liquids in the nonwoven fabric component of the laminate. The liquids absorbed in the nonwoven fabric can be contained by the liquid-resistant film to prevent or reduce liquid leakage from the laminate onto clothing, bedding or other surfaces contacting the outer film side opposite to the fabric side thereof. Also, the breathable laminate can permit passage of air from one direction only, which can be useful in applications where unidirectional air flow is desired across a sheet material.

The isolated thinning of the backing film layer in the breathable laminates of the present invention can be accomplished, in one embodiment, by extrusion lamination (coating) of backing film layer precursor polymeric material directly onto a surface of a nonwoven fabric comprising a mixed decitex fibre blend. Control of fabric surface and properties, such as nonwoven fabric fibre mix proportions, film coating thickness, and fibre size, permit the nonwoven fabric and backing film layer to be joined together with localized thinned regions and thicker regions introduced into the backing film layer. A film that otherwise would be vapor-impermeable or highly vapor-impermeable if extrusion laminated under similar conditions to a nonwoven fabric formed of only one size (decitex) fibres, can be transformed into a varied vapor-permeability film using a method of the present invention. A laminate made by such a method of an embodiment of the present invention combines comfort, e.g., breathability and absorbency, and a barrier property to liquids and microorganism penetration, even in a wet stage. Further, conventional, widely used, and more economical thermoplastics may be used for forming the film component of the breathable laminate of the present invention without requiring the use of relatively more expensive raw materials, such as specialty polymers having hydrophilic functionalities. Also, the breathable film component can be provided in the laminate without requiring the use of fillers or stretching techniques to impart breathability to the film.

The breathable laminates including these features can be used, for example, in disposable products, such as medical gowns, surgical drapes, disposable diapers, sanitary napkins, panty liners, underpads, wound care articles, wipes, or other medical, hygiene, or personal care products. As indicated, during use, the nonwoven fabric of the laminate, when used as a body side liner, can be in contact with or face the user of the laminate or a product incorporating the laminate. The breathable laminates also can be used in the construction industry, such as in housewrap, wall membranes, roofing membranes, or other building or construction membranes or sheeting.

The breathable laminates of the present invention can have a water vapor transmission rate (WVTR) of from 8 $g/m^2/24$ hours or greater, or from 10 $g/m^2/24$ hours or greater, or from 12 $g/m^2/24$ hours or greater, or from 14 $g/m^2/24$ hours or greater, or from 8 to 150 $g/m^2/24$ hours, or from 10 to 100 $g/m^2/24$ hours, or from 11 to 75 $g/m^2/24$ hours, or from 12 to 50 $g/m^2/24$ hours, or from 13 to 40 $g/m^2/24$ hours, or from 13 to 30 $g/m^2/24$ hours, or from 14 to 25 $g/m^2/24$ hours, or from 15 to 25 $g/m^2/24$ hours, or from 15 to 40 $g/m^2/24$ hours, or from 20 to 50 $g/m^2/24$ hours, or from 30 to 100 $g/m^2/24$ hours, or from 50 to 150 $g/m^2/24$ hours, as measured with vapor pressure applied from the nonwoven fabric side using the WVTR Test Procedures of ASTM E96-80 (testing out of direct contact with water, 32° C., RH50%), ISO 15106-3 (testing in direct contact with water), or both.

As explained, the indicated WVTR values reflect a measured value for the entire laminate. The backing film layer of the breathable laminate of the present invention has varied vapor permeability across the surface of the film. The breathable laminate can comprise a plurality of thinned localized regions and thicker regions, wherein the thinned localized regions are vapor-permeable and liquid-resistant and the thicker regions are vapor-impermeable and liquid-resistant. Therefore, the variation in vapor permeability can be a controlled or regulated variability with respect to areas defined by the thinned localized and thicker regions of the film, in conjunction with the adjoining mixed decitex nonwoven fabric component of the laminate. The backing film layer can comprise, for example, a total surface area (such as based on square distance units, e.g., $mm^2$) comprised from 1% to 30% of the thinned localized regions and 99% to 70% of the thicker regions, or from 2% to 25% of the thinned localized regions (total) and of 98% to 75% the thicker regions, or from 4% to 20% of the thinned localized regions and 96% to 80% of the thicker regions, or from 6% to 17% of the thinned localized regions and of 94% to 83% the thicker regions, or other percentages.

A breathable laminate of the present invention, in some embodiments, can have a water vapor transmission rate (WVTR), as measured as indicated above, of at least 5% or greater, or at least 7% or greater, or at least 10% or greater, or at least 15% or greater, or at least 20% or greater, or at least 30% or greater, or at least 40% or greater, or at least 50% or greater, or at least 60% or greater, as compared to a similarly made comparison laminate except that the comparative nonwoven fabric of the comparison laminate uses only the finer sized decitex fibres compared to the combination of the finer and coarser decitex fibres used in a nonwoven fabric of a laminate of the present invention.

In some embodiments, a breathable laminate of the present invention can have an air porosity (permeability), such as measured as indicated in the examples section herein with air pressure applied from the film side (or with suction drawn from the fabric side), of at least 0.5 liters/$m^2$/s, or at least 1 liters/$m^2$/s, or at least 1.5 liters/$m^2$/s, or at least 2 liters/$m^2$/s, or at least 2.5 liters/$m^2$/s, or from 0.5 liters/$m^2$/s to 5 liters/$m^2$/s, or from 1 liters/$m^2$/s to 3 liters/$m^2$/s, or from 1.5 liters/$m^2$/s to 2.8 liters/$m^2$/s. In some embodiments, the laminate of the present invention can have air porosity, as measured as indicated above (i.e., with film-side pressure or fabric-side suction), of at least 0.5 liters/$m^2$/s, or one of the other above-indicated air porosity ranges, and an opposite side air porosity (i.e., with fabric-side pressure or film-side suction) of less than 0.1 liters/$m^2$/s (e.g., 0 to 0.1 liters/$m^2$/s or 0 to 0.01 liters/$m^2$/s or 0 to 0.001 liters/$m^2$/s).

The breathable laminate of the present invention, in some embodiments, can have a hydrostatic head, as measured with water pressure applied to the film side, of 3 or more at 10 mbar/min, or 5 or more at 10 mbar/min, or 10 or more at 10 mbar/min, or 20 or more at 10 mbar/min, or 30 or more at 10 mbar/min, or 35 or more at 10 mbar/min, or from 5-100 at 10 mbar/min, or from 20-50 at 10 mbar/min. The breathable laminate can have a hydrostatic head, as measured with water pressure applied to the fabric side, of 3 or more at 10 mbar/min, or 5 or more at 10 mbar/min, or 10 or more at 10 mbar/min, or from 15 or more at 10 mbar/min, or from 3-50 at 10 mbar/min, or from 5-25 at 10 mbar/min, or from 10-20 at 10 mbar/min. A laminate comprising a liquid-resistant film according to some embodiments of the present invention can have a hydrostatic head value of at least 10% or greater, or at least 15% or greater, or at least 20% or greater, or at least 30% or greater, or at least 40% or greater, or at least 50% or greater, or at least 60% or greater, as compared to a non-laminate nonwoven fabric that comprises the indicated blend of mixed decitex fibres, as measured at 10 mbar/min (for both conditions of pressure applied from either the fabric side or the film side), using the Hydrostatic Head (HSH) Value Test Procedure described in the examples section herein.

The backing film layer used in the laminate of the present invention can comprise a flexible polymeric film material that forms at least a partial or complete barrier to the transfer of liquid through the film, but allows passage of vapors through the thinned localized areas/regions provided in the film by methods and constructions of the present invention. The backing film layer can be formed from an extrudable polymeric resin that can be formed into the flexible film and applied onto a nonwoven fabric surface. The extrudable polymeric resin that is extruded to form the polymeric film can be, for example, a thermoplastic resin, such as polyethylene, polypropylene, polyester, polyamide, polyethylene vinyl acetate, polyvinyl chloride, or polyvinylidene chloride, or any copolymers or physical blends thereof. The thermoplastic resin further can be, for example, a low density polyethylene (LDPE), linear low density polyethylene (LLDPE), polypropylene (PP), ethylene vinyl acetate (EVA), ethylene methacrylate (EMA), or any coextrusion or blend thereof. A homogenous film composition can be used in one embodiment.

The polymeric resin extruded to make the polymeric film can be combined with or contain conventional processing and performance additives used in film-forming polymer melts to the extent they do not impair the indicated formation of the vapor-permeable thinned localized regions or thicker vapor-impermeable regions in the liquid-resistant backing film that is directly extruded onto the surface of the mixed decitex nonwoven fabric. Conventional extrusion film additives, include, for example, colorants, UV inhibitors, flow promoters, and the like (in either liquid or pellet form). The additives, if used, can be mixed into the resin prior to arriving at the extrusion hopper.

In one embodiment, the polymeric film extruded from the polymeric resin on a surface of nonwoven fabric in accordance with the invention herein, has less than 2 vol %, or less than 1.5 vol %, or less than 1 vol %, or less than 0.5 vol %, internal porosity. As used herein, internal porosity refers to total internal air space defined within the bulk of the film between the outer major faces or sides of the film. In one embodiment, the vapor-permeable thinned localized regions of the backing film layer differ in film thickness, i.e., have a smaller film thickness, at such regions from the thicker regions of the backing film layer by at least 10% or more, or at least 15% or more, or at least 25% or more, or at least 50% or more.

The different decitex fibres used in the nonwoven fabric can have a decitex of from 0.5 to 15, and the first decitex and second decitex fibres used can differ by at least 1 decitex, or differ by at least 2 decitex, or differ by at least 3 decitex, or differ by at least 4 decitex. Also, the first decitex fibres can have a decitex of from 3.5 to 15 and the second decitex fibres can have a decitex of from 0.5 to 3.5, or the first decitex fibres can have a decitex of from 4 to 12 and the second decitex fibres can have a decitex from 0.8 to 3.5, or the first decitex fibres can have a decitex from 5 to 8.5 and the second decitex fibres can have a decitex of from 1 to 2.5, or the first decitex fibres can have a decitex of from 5.5 to 8 and the second decitex fibres can have a decitex of from 1.5 to 2.25. Although illustrated herein as combining two different decitex fibres, the fibre blend used in making the nonwoven fabric optionally can comprise one or more additional fibres having a decitex that differs from both the first decitex and second decitex fibres.

The fibre materials used for each of the different decitex fibres in the nonwoven fabric can be synthetic or natural. Synthetic fibre materials that can be used include, for example, synthetic polymeric fibres such as polyester (e.g., polyethylene terephthalate), rayon (e.g., viscose rayon), polyolefin (e.g., polyethylene, polypropylene), polyacrylate, or any copolymers or combinations thereof. The fibres having differing decitex used to form the nonwoven fabric can comprise, for example, the same or different type of fibre material. Benefits can be associated with using coarser (thicker) fibres that are formed of a different polymer than the finer (thinner) fibres, such as by providing differential polymer flow during film extrusion lamination when the film polymer is still in molten state. Homogenous fibres, multicomponent fibres (e.g., sheath-core fibres, bicomponent fibres, conjugate fibres), or any combinations thereof, can be used.

The nonwoven fabric having mixed decitex fibres can incorporate loose fibres (e.g., formed meltblown fibres or chopped continuous filaments). Generally, in a conventional meltblown process, a molten polymer is extruded under pressure through orifices in a spinneret or die. High velocity air impinges upon and entrains the molten polymeric filaments as they exit the die. The energy of this step is such that the formed filaments are greatly reduced in diameter and are fractured so that fibres of finite length are produced (i.e., meltblown fibres). This differs from the spunbond process whereby the continuity of the filaments being spun into the web is essentially preserved. Bales of first decitex fibres and second decitex fibres formed in such manners can be thoroughly mixed in an air mixing chamber, and then either carded to form a carded web or randomly laid on a foraminous forming structure to form a nonwoven web that can be consolidated and further processed in manners such as described herein.

Alternatively, the mixed decitex fibres used in the nonwoven fabric can comprise fibres that are continuous filament layers. The continuous filaments can be manufactured by a conventional "spunbond" process. A spunbond process involves supplying a molten polymer, which is then extruded under pressure through a large number of orifices in a plate known as a spinneret or die. The resulting continuous filaments are quenched and drawn by any of a number of methods, such as slot draw systems, attenuator guns, or Godet rolls. The continuous filaments are collected as a loose web upon a moving foraminous surface, such as a wire mesh conveyor belt. To provide a nonwoven web formed of continuous filaments having different decitex, more than one spinneret can be used to simultaneously extrude different filaments from different spinnerets having different sizes (decitex). Substantially continuous filaments also can be used where continuous filaments have been cut into relatively long segments, such as 0.6 meter or longer.

The process to form either a single layer or a multiple-layer nonwoven fabric can be continuous, that is, the process steps can be uninterrupted from extrusion of the filaments to form the first layer until the consolidated fabric or web is extrusion coated with the backing film layer, and the resulting composite laminate wound into a roll.

In one illustrative embodiment, the fibre blend used in forming the nonwoven fabric can comprise, for example, a blend of 10% to 90% by weight polyester fibres and from 90% to 10% by weight viscose rayon fibres, or from 20% to 80% by weight polyester fibres and from 80% to 20% by weight viscose rayon fibres, or from 30% to 70% by weight polyester fibres and from 70% to 30% by weight viscose rayon fibres, or from 35% to 65% by weight polyester fibres and from 65% to 35% by weight viscose rayon fibres, or from 40% to 60% by weight polyester fibres and from 60% to 40% by weight viscose rayon fibres. The nonwoven fabric comprising any of these blend ratios further can comprise, for example, polyester fibres having a decitex of from 5 to 8.5 and viscose rayon fibres having a decitex of from 1 to 2.5. When the first and second fibres of the nonwoven fabric are loose (e.g., staple fibres), the loose fibres independently can have a length, for example, of from 1 mm to 500 mm, or a length from 5 mm to 250 mm, or a length of from 10 mm to 150 mm, or a length of from 15 mm to 100 mm, or a length of from 20 mm to 75 mm, or a length of from 25 mm to 50 mm.

The blend of fibres also can contain conventional additives to the extent they do not impair the indicated formation of the vapor-permeable thinned localized regions in the backing layer film that is formed by extrusion lamination on a surface of the nonwoven fabric. For example, the fibres can optionally include processing and performance additives introduced internally during manufacture of the fibre and/or surface coated upon the fibres as a post-treatment. Internal fibre additives include, for example, colorants (e.g., inorganic pigments, organic pigments, dyes), fillers, surfactants, wetting agents, u.v. stabilizers, antioxidants, or combinations thereof. Surface coatings can include, for example, fire retardants, surfactants, wetting agents, or combinations thereof.

The nonwoven fabric also can have a multilayered fibrous construction comprising a nonwoven fabric layer directly adjacent the backing film layer which contains the blend of first and second decitex fibres, and one or more additional nonwoven fabric layers arranged on the opposite side of the nonwoven fabric containing mixed decitex fibres to the backing film layer. For example, a second nonwoven fabric layer can be included which is separated from the backing film layer by the a first nonwoven fabric layer containing first and second decitex fibres, wherein the first nonwoven fabric layer is the blend of first decitex fibres and second decitex fibres that differ by at least 1 decitex, and the second nonwoven fabric layer is a second blend of first decitex fibres and second decitex fibres that may be the same or different in decitex. For example, the second nonwoven fabric layer can comprise, for example, a blend of fibres in a range of from 0.5 to 15 decitex wherein all the fibres thereof differ in decitex by less than 0.25 decitex.

The nonwoven fabrics of the present invention can be formed using conventional processes including, for example, consolidation by hydroentanglement, thermobonding, chemical bonding, mechanical bonding (e.g., carding), or any combinations thereof. In these manufacturing processes, the initial process step can be the formation of a web of loose (i.e., staple) first decitex and second decitex fibres, such as indicated for continuous and loose (e.g., staple) fibres. In general, a consolidated nonwoven fabric is provided with sufficient structural integrity to tolerate the extrusion lamination processing such as described herein.

As a consolidation process using hydroentanglement and/or chemical bonding, the nonwoven fabric having first decitex and second decitex fibres can be hydroentangled and treated with a binder composition before the extrusion lamination of the backing film layer thereon. For example, a web of first decitex and second decitex fibres can be formed as above and passed through a hydroentanglement station, such as a single side belt entangler, a hydroentangling forming drum, or both, equipped with a series of water spray nozzles, which are capable of hydraulically entangling the fibres. The entangled web can be then de-watered and fed into a binder printing station where a binder is added to the nonwoven fabric. The nonwoven fabric containing the binder can be then dried and cured in an oven. The binder can comprise a binder material selected from, for example, at least one of acrylic, ethylene vinyl acetate, vinyl-acrylic, and styrene-butadiene rubber based binder, or any combinations thereof. The binder can comprise, for example, an aqueous solution of an acrylic or ethylene vinyl acetate (EVA) type of binder. Single binder coatings or separate coatings of different types of binders can be added to the nonwoven fabric by impregnation, printing, or coating, for example. The proportion of binder added to the nonwoven fabric can be, for example, from 2.5% to 30% by weight relative to the total weight of the nonwoven fabric. Conventional additives can be included in the binder added to the nonwoven fabric. For example, pigments optionally can be included in the binder added to the nonwoven fabric.

When using a thermobonding process for consolidation of the nonwoven fabric, thermal point bonding can be used where a web of the first decitex and second decitex fibres to be bonded can be passed between a flat anvil roll and a heated embossing roll or patterned calender roll, which bond the fibres to stabilise the web into a nonwoven fabric. An alternative thermobonding process can involve forcing heated air through the web to melt a fusible binder component thereof, and is generally known as a through-air bonding process. The fibrous web can be sprayed with powdered polymers of low melting point under vacuum and then through-air bonded in an oven, or the binder component may be fibres instead of powdered polymers.

The breathable laminate formed in accordance with the invention can comprise a backing film layer that has a basis weight of from 12 to 30 grams per square meter and a nonwoven fabric that has a basis weight of from 25 to 120 grams per square meters, or a film from 15 to 25 grams per square meter and a nonwoven fabric having a basis weight of from 40 to 100 grams per square meter, or a film from 18 to 23 grams per square meter and the nonwoven fabric having a basis weight of from 50 to 75 grams per square meter. As indicated, the nonwoven fabric can have a multilayered construction wherein at least one layer thereof that adjoins the backing film layer contains a first decitex and second fibre blend. These weights of the nonwoven fabric can apply to a nonwoven fabric formed exclusively of first and second decitex fibres, or such a layer in combination with other nonwoven fabric layers that do not necessarily comprise first decitex and second decitex fibre blends.

The backing film layer in the finished breathable laminate can have a thickness, for example, of from 0.03 to 0.3 mm, and the nonwoven fabric can have a total thickness, for example, of from 0.25 to 1.25 mm.

The backing film layer is co-extensively in direct contact with the nonwoven fabric over a predominant surface area of the nonwoven fabric, such as at least 50%, or at least 75%, or at least 90%, or at least 95%, or at least 99%, of the opposing surface areas of the backing film layer and nonwoven fabric. The co-extensive direct contact provided between the backing film layer and the nonwoven fabric can include the geometric central regions of the respective facing components. For example, where the backing film layer and nonwoven fabric have respective length and width dimensions in sheet forms of the materials, the backing film layer and nonwoven fabric components include directly attached midway regions relative to the width and/or length dimensions of the two components.

The direct attachment of the backing film layer to the nonwoven fabric having first decitex and second decitex fibres to form a laminate having varied breathability can be accomplished exclusively by the interactions of the backing film layer as extrusion coated onto a surface of the first decitex and second decitex fibre containing nonwoven fabric. For example, these interactions can occur at the nip region of a pair of pressure rolls followed by a film cooling mechanism (such as using a chill roll or other cooling means), and without use of specialty polymers in the film, film additives, and/or stretching processes.

A method of making the breathable laminate can include steps of extruding a film comprising a thermoplastic resin-containing composition directly onto a nonwoven fabric to provide a breathable laminate, wherein the nonwoven fabric comprises a blend of first decitex fibres and second decitex fibres in a range of from 0.5 to 15 decitex and wherein the first decitex fibres and the second decitex fibres differ by at least 1 decitex. The first decitex and second decitex fibres can have respective differing decitex range values and can be present in the blend in proportions such as indicated elsewhere herein. After the film is extruded onto a surface of the nonwoven fabric containing first decitex and second decitex fibres, the film layer and nonwoven fabric are bonded, e.g., by thermal bonding using pressure rolls, such as nip rolls, and the laminate can be cooled or chilled to produce a breathable laminate of the invention. The blend of first decitex and second decitex fibres interact with the liquid-resistant backing film layer extruded thereon to form vapor-permeable, liquid-resistant thinned localized regions in the backing film layer that permanently remain after cooling the nonwoven fabric having the film layer extruded thereon.

A representative direct extrusion film process is as follows. Blending and dosing storage can comprise at least one hopper loader for thermoplastic polymer resin chips or pellets, and optionally any additive or additives, which hopper or hoppers feed the chips or pellets into variable speed augers. The variable speed augers can transfer predetermined amounts of polymer resin chip or pellets and any additives into a mixing hopper. The mixing hopper can contain a mixing propeller that when activated can further enhance the homogeneity of the mixture. The mixed polymer resin chips or pellets and any additives can be fed into a multi-zone extruder. Upon mixing and extrusion from a multi-zone extruder, the flowable polymer compound can be conveyed via heated polymer piping through a screen changer, wherein breaker plates having different screen meshes are employed to retain solid or semi-molten polymer resin chips or pellets and other macroscopic debris. The mixed polymer then can be fed into a melt pump, and then directly to an extrusion die or via an optional combining block. A combining block, if used, allows for multiple film layers to be extruded, where the film layers being of either the same composition or different compositions, if fed from different systems as described above. The combining block, if used, is connected to an extrusion die. The extrusion die is positioned in an overhead orientation such that molten film is deposited onto an upper surface of the nonwoven fabric having first decitex and second decitex fibres and the nonwoven fabric and film extruded thereon can pass through a set of nip or pressure rolls for bonding.

The polymeric material extruded by the die comprises the thermoplastic-resin containing composition in a flowable state. Lamination of the film layer containing the polymeric material to the nonwoven fabric can be performed by passing the fabric onto which the film layer is extruded through the nip region of pressure rolls to form strong adhesion (i.e., good lamination). The temperature at which the polymeric resin is extruded may vary depending on the composition of the film material. For example, a low density polyethylene (i.e., LDPE) thermoplastic resin-containing composition can be extruded at a temperature greater than 300° C. The thermoplastic resin-containing composition can be extruded from a slit die with a die opening effective to allow a thin continuous film to be coated onto a surface of the nonwoven fabric. The die opening can be, for example, from 0.5 mm to 0.8 mm, such as used for extruding LDPE at a temperature greater than 300° C. A chill roll can be used to cause the extruded film to cool at a controlled rate. For example, one of the pressure rolls forming a nip region at which the film layer can be bonded to the nonwoven fabric, for example, also can be positioned opposite to a chill roll through which the resin film coated-nonwoven fabric can be conveyed. The chill roll can be kept at a temperature, for example, of less than 32° C., or less than 25° C., or less than 20° C., during the film layer cooling process. The chill roll surface design can be varied to provide different air permeability properties, for example, the chill roll may have a matte chromium plated surface. The parameters such as the composition of the blend of first decitex and second decitex fibres in the nonwoven fabric, the extruded film composition, the extruded film temperature upon die exit, die opening size and configuration, and extrusion rate can be controlled such that the thinned localized regions are permanently formed in the breathable laminate once cooled. Illustrative combinations of these parameters are included in the examples, but are not limited thereto.

Although illustrated herein as a backing film layer and single accompanying nonwoven fabric, the breathable laminates of the present invention also can have other layers. For example, the film can be sandwiched in-between nonwoven fabric layers having same or different properties and attached on each side of the film layer. This configuration can achieve air permeability and/or absorbency from one or both sides. Also, in another configuration, the film can be extruded to be sandwiched in-between a nonwoven fabric and a foam layer. The foam layer and the nonwoven fabric can absorb liquids and the backing film layer can form a liquid barrier to contain the liquids while permitting gases and vapors to pass or "breath" through from either the nonwoven fabric or the foam layer side.

The present invention will be further clarified by the following examples, which are intended to be only exemplary of the present invention.

EXAMPLES

Example 1

The nonwoven fabric samples A and 1, described in further detail below, were measured for air porosity performance, hydrostatic head performance, burst strength performance, barrier index performance, tensile strength performance, absorption performance, delamination strength performance, and water vapor transmission rate (WVTR), in accordance with the respective test methods described below.

Test Methods:
Air Porosity (Test method ENISO 9237: 1995).
Hydrostatic Head (Test method EN20811: 1992).
Water Vapor Transmission Rate (Test Method(s) ASTM E96-80; ISO 15106-3).
Burst Strength (Test method EN 13938-1: 1999).
Barrier Index (Test method ISO 22610: 2006).
Tensile Strength (Test method EN29073-3: 1992).
Absorption (Test method EN29073 part 6 (drainage with support on 120 mm² metal frame)).
Absorption (Test method EN29073 part 6 (drainage with cylindrical wire basket)).
Delamination Strength:
To determine the delamination strength of a laminated nonwoven, the following materials and procedures are used.

1. Equipment:
Cutting board & Cutting die; Instron tensile tester, model 1026; Jaw gap: 10 cm; Jaw clamp width: 5 cm; Jaw traverse speed: 100 mm/min.

2. Sampling and Testing Procedure:
Cut out 5 pieces of laminated sample for each direction (machine and cross direction), according to standard method ERT 130.2 (1999). They must be cut out clearly, (50±0.5) mm wide and minimum 250 mm long. De-laminate the laminated material for approximately 12 cm. Place the de-laminated ends between the jaws of the tensile machine, these being 10 cm apart. The test piece should be as straight as possible without applying pretension. Apply a constant rate of extension of 100 mm/min for 100 mm distance and record the average force (available as software package from Instron to calculate the average force). Discard the results from any test piece where the break occurs in the clamp. Carry out the operation 5 times for each direction. Determine the mean of each characteristic and the standard deviation of the results as required.

3. Test Conditions:

Relative humidity: 65%±2%, Temperature: 20°±2° Celsius.

Water Vapor Transmission Rate (WVTR):

As indicated, WVTR can be determined by ASTM E96-80 and ISO 15106-3.

ASTM E96-80: "Standard Test Methods for Water Vapor Transmission of Materials", water method, procedure D (50% RH & 32° C.), which provides a best simulation to a condition of use of a gown material constructed of a sample material under humid condition, but not in direct contact with perspiration sweat or water.

For purposes of ASTM E96-80, water vapor transmission is a measure of how much water vapor will pass through a material per unit area per unit time. Testing is performed by sealing a specimen to the open mouth of a test dish containing either desiccant or water and placing the assembly into a controlled atmosphere. The test unit is weighed periodically and the weight is plotted as a function of time. Water vapor transmission is taken as the slope of the curve (in the linear region) divided by the area of the dish opening. For example, in plotting weight gain (G) (ordinate value) with respect to time tested (t)(abscissa value) for the WVT data, initial data may be non-linear followed by data showing a linear relationship between the G and t data, as a function of increasing test time, which linear portion of the plotted data is used for the WVT calculation. Rate of Water Vapor Transmission (g/h·m$^2$) is calculated using the formula: WVT=G/t/A=(G/t)/A, where G is the weight gain, t is the time tested, and A is the area of the test area (area of dish opening).

ISO 15106-3: "Standard Test Method for Water Vapor Transmission Rate, Part 3", uses an electrolytic detection sensor method and the electrolytic principle provides high sensitivity and high precision/accuracy data. This electrolytic detection sensor method is also chosen with a test condition of direct contact with water and 23° C. This condition simulates the gown material constructed of a sample material when it is in direct contact with perspiration sweat or water.

In determination of water vapor transmission rate according to part 3 (electrolytic detection sensor method) of ISO 15106-3, the specimen is clamped in between dry and humid chambers saturated saline or defined sulphuric acid solutions or water. Due to the humidity difference between the two sides of the specimen, water vapor permeates from high humidity chamber to the low one. And in the low humidity chamber, water vapor is brought to sensor by dry carrier gas; at the meantime, the sensor generates electrolytic signals. By analyzing and calculating those signals, the water vapor transmission rate in grams per square meter 24 hours (g/m$^2$·24 hr or g/m$^2$·day or g/m$^2$·d) can be determined.

Nonwoven Fabric 1

A 66 grams per square meter (g/m$^2$) basis weight nonwoven fabric sample 1 was produced by hydroentangling two layers of dissimilar carded fibre blends, and binder printing and drying the nonwoven. The process 100 used for making nonwoven fabric sample 1 is generally shown in FIG. 1. A first nonwoven layer ("Layer 1") included 65%, by weight, viscose rayon staple fibres, and 35%, by weight, polyester staple fibres, and a second nonwoven layer ("Layer 2") included 65%, by weight, polyester staple fibres and 35% by weight, viscose rayon staple fibres. The viscose rayon fibre for Layers 1 and 2 was obtained from Lenzing under the product name Lenzing Viscose Rayon TD (decitex 1.7, staple length 40 mm, diameter: 12.52 μm, specific gravity: 1.38 g/cm$^3$). The polyester fibre of Layer 1 was obtained under the product name DACRON polyethylene terephthalate NSD 158 (decitex 1.7, staple length 38 mm, diameter: 12.52 μm) from ADVANSA GmbH, Hamm, Germany, which fibre is referred to as "PET-Finer" in Tables 1-2. The polyester fibre of Layer 2 was obtained under the product name DACRON polyethylene terephthalate 54-NSD (decitex 6.7, staple length 38 mm, diameter: 24.86 μm, s.g.: 1.38 g/cm$^3$) from ADVANSA GmbH, Hamm, Germany, which fibre is referred to as "PET-Coarser" in Tables 1-2. Layer 2 was a mixed decitex fibre layer. The formula used for calculation of fibre diameter was as follows:

$$\varnothing = [(4 \times 10^{-6} \cdot dtex)/\pi\rho]^{1/2}$$

where ρ represents the fibre material's density in grams per cubic centimeter, and the calculated diameter is in cm, which was converted to μm (1 cm=10,000 μm).

The two separate types of fibrous blends were fed to carding units 101 and 102. The carded staple fibre blend from the last carding unit 102 was a 30 g/m$^2$ web collected onto a conventional formation belt as Layer 2 and advanced toward the first carding unit 101 where the 30.5 g/m$^2$ carded staple fibre blend from the first carding unit, Layer 1, was collected on the surface of the carded staple fibre blend of Layer 2. Layer 1 from card 1 is laid on Layer 2 from card 2. The layered carded staple fibre blends 110 where slightly condensed and advanced onto a single side belt hydroentangler unit 103. The slightly condensed carded staple fibre blends were entangled together with a jet water pressure sequence of 4×40 bars, i.e., a sequence of 40, 40, 40, 40 bars. With respect to the hydroentangling station set-up, the forming wire material was polyester monofilament; Weave Pattern=Plain; Ø Warp & Shute=0.45 mm; number of warp wire=14.2/cm; number of Shute wire=11.8/cm; belt thickness 0.75 mm; open area=22.9%; air permeability=3350 cm$^3$/second); drilled orifice size and spacing of strips, hole size=0.005"; holes per inch=50.

The entangled fibrous matt was subsequently passed through a wet-out unit 104, and printed at print unit 105 with an aqueous solution of soft ethylene vinyl acetate (EVA) binder on the belt-side (Layer 1 side) of the fabric, and dried on a stack of drying cans 106. The EVA binder add-on from print unit 105 was 2 grams per square meter (g/m$^2$) dry on dry. An aqueous solution of hard vinyl acetate (VA) polymer binder, including light green colour pigment, was printed on the non-belt side (Layer 2 side) of the fabric from print unit 107. The VA binder add-on was 3.5 grams per square meter (g/m$^2$) dry on dry. The resultant fabric was then dried and cured on two stacks of drying cans 108, and the dried and cured fabric 111 wound into a roll at the winding station 109. In this manner, the nonwoven fabric sample 1 was developed with a fabric surface (from Layer 2) having 65% coarse polyester fibre at 6.7 Dtex/38 mm and 35% viscose rayon 1.7 Dtex/40 mm. The nonwoven fabric surface was modified with the hard vinyl acetate polymer binder as fabric finish so as to keep the surface feature with minimum deformation during extrusion lamination. The relatively small amount of ethylene vinyl acetate binder was used to control the hairiness on the other side of the nonwoven fabric and is penetrated slightly into the fabric structure to give further stability to the fabric composition and yet maintain softness. The composition of nonwoven fabric sample 1 is summarized in Table 1.

TABLE 1

| Basis weight (or print rate) (g/m$^2$) | Material |
| --- | --- |
| 30.5 | Layer 1 |
| 30 | Layer 2 |
| 2 | Soft EVA binder |
| 3.5 | Hard VA binder on Layer 2 surface |
| 66 | Total NWF weight |

TABLE 1-continued

| Basis weight (g/m²) | Layer 1 | % (wt) |
|---|---|---|
| 19.8 | Viscose Rayon | 65 |
| 10.7 | PET - Finer | 35 |
| 30.5 | Fibre Weight - Layer 1 | 100 |

| Basis weight (g/m²) | Layer 2 | % (wt) |
|---|---|---|
| 19.5 | PET - Coarser | 65 |
| 10.5 | Viscose Rayon | 35 |
| 30 | Fibre Weight - Layer 2 | 100 |

Figure 2:
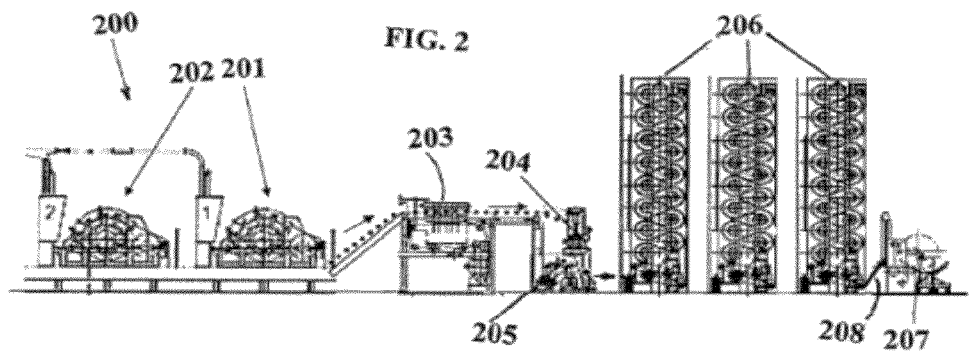
FIG. 2 is a schematic view of an equipment arrangement for making a nonwoven fabric of a comparison laminate.

Nonwoven Fabric A:

The process 200 used for making nonwoven fabric sample A is generally shown in FIG. 2. A 55 grams per square meter (g/m²) carded, staple fibre blend of viscose rayon and polyester fibres was formed by hydroentangling a carded, staple fibre blend of 58%, by weight, viscose rayon and 31%, by weight, polyester fibres, and binder printing and drying the nonwoven fabric. The viscose rayon fibre was obtained from Lenzing under the product name Lenzing Viscose Rayon TD (decitex 1.7, staple length 40 mm, diameter: 12.52 µm, s.g.: 1.38 g/cm³). The polyester fibre was obtained under the product name DACRON polyethylene terephthalate NSD 158 (decitex 1.7, staple length 38 mm, diameter: 12.52 µm, s.g.: 1.38 g/cm³) from ADVANSA GmbH, Hamm, Germany, which fibre is referred to as "PET-Finer" in Table 2. A carded, staple fibre blend of 58%, by weight, viscose rayon and 31%, by weight, polyester fibres was fed from an opener to cards 201 and 202 as shown in FIG. 2. The fibrous matt was advanced on a belt fed to hydroentanglement unit 203, a single side belt entangler, and entangled with a jet water pressure sequence of 4×40 bars. The fabric was subsequently printed at print unit 204 on the non-belt side with 3 grams/m² of acrylic binder, including dark green colour pigment. Another 3 grams/m² of the pigmented acrylic binder, including dark green colour pigment, was printed on the opposite belt side of the fabric at print unit 205. The acrylic binder was obtained from BASF under the product name ACRONAL LA 471 S. The resultant fabric was then dried and cured on three stacks of drying cans 206, and then dried and cured fabric 208 wound into a roll at the winding station 207. The composition of nonwoven fabric sample A is shown in Table 2.

TABLE 2

| Basis weight (or print rate) (g/m²) | Material | % (wt) |
|---|---|---|
| 32 | Viscose Rayon | 58 |
| 17 | PET - Finer | 31 |
| 6 | Acrylic Binder | 11 |
| 55 | Total NWF Weight | 100 |

Figure 3:
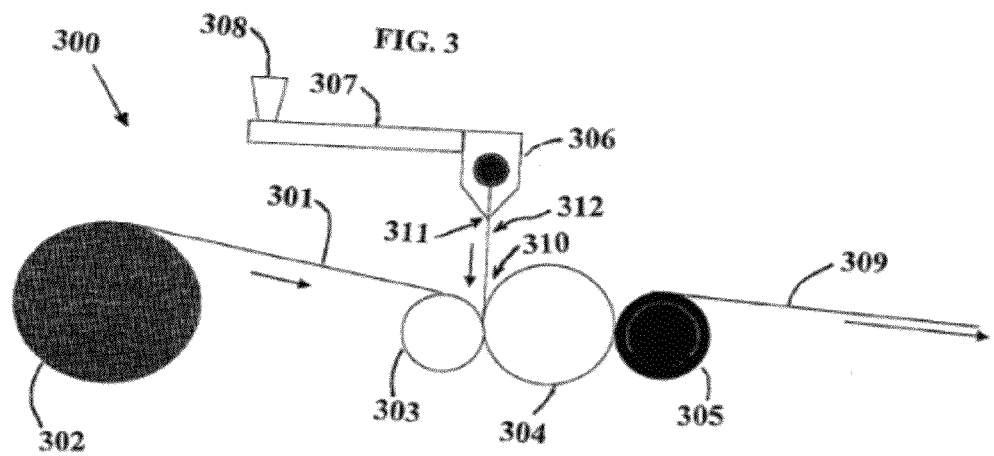
FIG. 3 is a schematic view of an extrusion lamination equipment arrangement for making a breathable laminate in accordance with an embodiment of the present invention.

The nonwoven fabric samples 1 and A were further coated off-line with 20 grams per square meter (g/m²) of low density polyethylene (LDPE) film using an extrusion process. Nonwoven fabric sample 1 was coated on the Layer 2 side thereof (i.e., the side with coarser PET fibre). The extrusion lamination method used is generally shown as process 300 in FIG. 3. During the extrusion lamination process, the nonwoven fabric 301 was unwound from an unwind station 302 and advanced through nonwoven web tension control guide rolls at a rate of 95 m/min to the nip 310 defined by a pair of pressure rolls 303 and 304 positioned below an extrusion die 306. Thermoplastic resin pellets were fed into an in-feed hopper 308 for introduction to feeding screw 307. The resin pellets were heated and softened into a flowable mass in feeding screw 307 and introduced into extrusion die 306. The extrusion die 306 had a discharge opening 311. A thin uniform coating of LDPE resin 312 was extruded from the extrusion die 306 directly onto the nonwoven fabric 301 in the form of a continuous film. The melted resin was extruded directly onto the nonwoven fabric in the form of a film. The LDPE resin extruded onto the nonwoven fabric was obtained under the product name LDPE LD 259 from ExxonMobil™. The LDPE resin had a melt temperature of 103° C., Melt Index of 12 g/10 min, and density of 0.915 g/cc. After passing through pressure rolls 303 and 304, the extrusion laminated nonwoven fabric was immediately conveyed between pressure roll 304 and chill roll 305 (surface temperature: 30° C.), and then the cooled laminate product 309 was fed to a winding station (not shown).

A summary of the properties determined for the laminates formed with the nonwoven fabric 1 (i.e., "7121" or "7121 F") and the nonwoven fabric A (i.e., comparison laminate "7327" or "7327 F") are shown in Tables 3-5. Table 3 is shown in FIG. 14. As indicated in the tables, multiple samples of each type of nonwoven fabric were tested for some of the property determinations. The arrows in the diagrams in Table 3 showing the construct of the film ("FILM" or "▬") and nonwoven fabric ("NWF" or "###") indicate the direction of airflow through the construct for the air porosity test, the direction of water flow for the HSH test and burst strength test, the side of the laminate from which water is received or contacted for the water vapor transmission tests. Tables 3-5 show individual and average values for multiple sample tests (e.g., WVTR), and film and fabric weight calculation information. Table 3 shows data for several functional properties that may be relevant to medical gown or other uses, and Tables 4 and 5 show data for other properties determined for the laminates.

TABLE 4

| | | Light Green (7121) Before Calender | Dark Green (7327) | Light Green (7121) After Calendering P130 (40 bars -Cold) | Dark Green (7327) |
|---|---|---|---|---|---|
| Bulk (mm/ply) EN29073 part2) | | 0.456 | 0.424 | 0.355 | 0.329 |
| | | 0.467 | 0.408 | 0.378 | 0.341 |
| | | 0.469 | 0.417 | 0.348 | 0.339 |
| | average | 0.464 | 0.416 | 0.360 | 0.336 |
| Tensile MO N/50 mm/ply EN29073-3: 1992 | | 113 | 109 | 128 | 107 |
| | | 116 | 118 | 123 | 107 |
| | | 119 | 119 | 128 | 104 |
| | | 109 | 110 | 125 | 110 |
| | | 105 | 116 | 129 | 100 |
| | | 121 | 108 | 130 | 104 |
| | average | 114 | 113 | 127 | 105 |
| Tensile CD N/50 mm/ply EN29073-3: 1992 | | 16 | 14 | 18 | 15 |
| | | 18 | 13 | 15 | 18 |
| | | 14 | 11 | 14 | 14 |
| | | 16 | 12 | 17 | 19 |
| | | 13 | 15 | 18 | 15 |
| | | 18 | 17 | 17 | 18 |
| | average | 16 | 14 | 16.5 | 17 |
| De-Lamination Strength (at Peak) | | | | | |
| MD | | 0.43 | 2.01 | 1.12 | 0.98 |
| | | 0.36 | 2.34 | 0.97 | 0.88 |
| | | 0.41 | 2.2 | 0.86 | 1.02 |
| | | 0.44 | 2.54 | 1.21 | 0.94 |
| | | 0.47 | 2.34 | 1.42 | 1.02 |
| | | 0.4 | 2.44 | 1.02 | 1.14 |
| | average | 0.42 | 2.31 | 1.10 | 1.00 |

TABLE 4-continued

|  | Light Green (7121) Before Calender | Dark Green (7327) Before Calender | Light Green (7121) After Calendering P130 (40 bars -Cold) | Dark Green (7327) After Calendering P130 (40 bars -Cold) |
|---|---|---|---|---|
| CD | 0.45 | 0.88 | 1.03 | 0.74 |
|  | 0.36 | 0.87 | 1.05 | 0.87 |
|  | 0.48 | 0.86 | 0.86 | 0.77 |
|  | 0.38 | 0.88 | 1.02 | 0.84 |
|  | 0.44 | 0.76 | 1.32 | 0.72 |
|  | 0.46 | 0.74 | 1.29 | 0.85 |
| average | 0.43 | 0.83 | 1.10 | 0.80 |

TABLE 5

|  | Light Green (7121) Before Calender | Dark Green (7327) Before Calender | Light Green (7121) After Calendering P130 (40 bars -Cold) | Dark Green (7327) After Calendering P130 (40 bars -Cold) |
|---|---|---|---|---|
| Absorption--PGI TM 1075 EM29073 part 6 (drainage with support on 120 mm² metal frame) | 438 | 510 | 440 | 438 |
|  | 454 | 490 | 444 | 454 |
|  | 450 | 485 | 450 | 500 |
|  | 432 | 525 | 425 | 517 |
|  | 466 | 490 | 466 | 466 |
| average | 448 | 500 | 445 | 475 |
| Absorption--PGI TM 1016 EN29073 part 6 (drainage with cylindrical wire basket) | 640 | 610 | 610 | 610 |
|  | 670 | 650 | 630 | 625 |
|  | 700 | 680 | 590 | 590 |
|  | 640 | 600 | 600 | 590 |
|  | 650 | 660 | 670 | 660 |
| average | 660 | 640 | 620 | 615 |
| Film Weight (g/m²) measured from delaminated film | 19.9 | 20.5 |  |  |
|  | 20.20 | 19.81 |  |  |
|  | 19.87 | 20.07 |  |  |
|  | 19.80 | 20.12 |  |  |
|  | 20.14 | 19.85 |  |  |
|  | 20.05 | 19.88 |  |  |
| average | 19.99 | 20.04 |  |  |
| Film Thickness (mm/ply) measured from delaminated film ERT 30.5-99 | 0.09 | 0.05 |  |  |
|  | 0.09 | 0.04 |  |  |
|  | 0.10 | 0.06 |  |  |
|  | 0.13 | 0.05 |  |  |
|  | 0.14 | 0.08 |  |  |
|  | 0.11 | 0.05 |  |  |
| average | 0.11 | 0.06 |  |  |
| NWF + Film (Thickness mm/ply) | 0.464 | 0.416 |  |  |
|  | 0.450 | 0.414 |  |  |
|  | 0.515 | 0.426 |  |  |
|  | 0.444 | 0.408 |  |  |
|  | 0.475 | 0.426 |  |  |
|  | 0.445 | 0.425 |  |  |
| average | 0.466 | 0.419 |  |  |
| Actual NWF + Film weight g/m² | 86.94 | 76.74 |  |  |
| NWF (g/m²): | 66 | 55 |  |  |
| Film (g/m²) | 18.5 | 18.5 |  |  |
| Theoretical NWF + Film weight g/m² | 84.5 | 73.5 |  |  |

Figure 4:
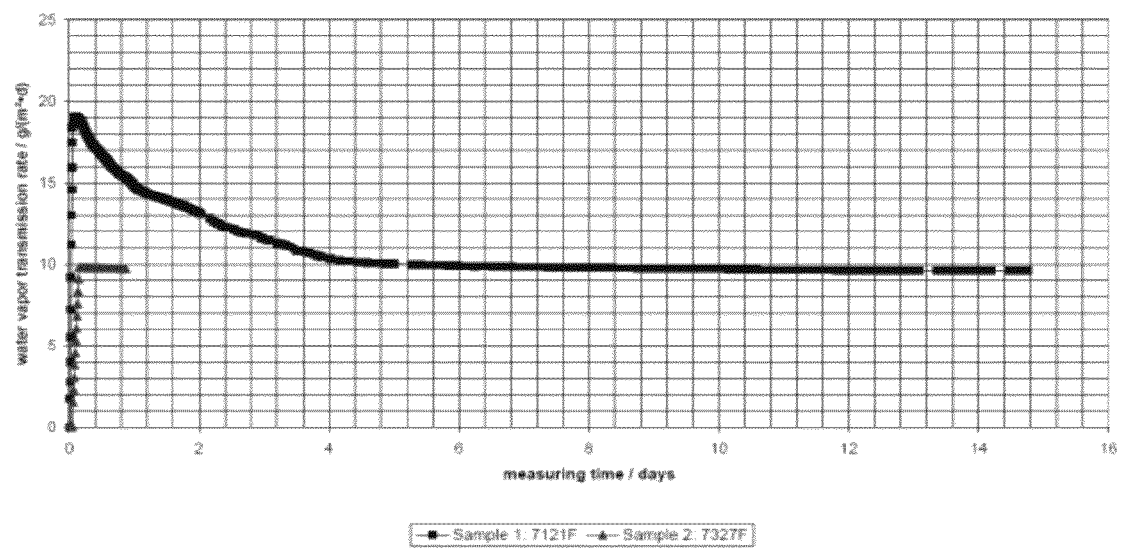
FIG. 4 is a graph showing water vapor transmission rate over a measuring time for breathable laminate in accordance with an embodiment of the present invention and a comparison laminate.

The results in Tables 3-5 show the laminate 7121F, including the mixed decitex fibre layer in the laminate, exhibited significantly greater water vapor transmission, as determined by standard ISO 15106-3 (in contact with water) than the comparison sample 7327F having a same decitex fibre layer only for the nonwoven portion of the laminate (i.e., average values of 16.5 g/m²·day versus 10.2 g/m²·day), without sacrificing physical properties useful for the laminate. As further shown in FIG. 4, which is a graph showing water vapor transmission rates over measuring times that were determined for the first listed samples of 7121F and 7327F in Table 4 for WVTR measured by ISO 15106-3, the WVTR of the 7121F sample (sample 1), which was measured for 14+ days, immediately shows a peak WVTR of approximately 19 grams/m²/24 hours, which slowly decreases to approximately 10 grams/m²/24 hours by about day 4, after which the WVTR stayed relatively constant at approximately 10 grams/m²/24 hours up to and beyond the 14th day of measurement. The WVTR of the 7327F sample (sample 2), which was measured for approximately one day, showed a different profile from 7121F. The WVTR of the 7327F sample reached a lower peak value, at approximately 10 grams/m²/24 hours, than the 7121F sample, and more slowly than the 7121F sample. These results indicate that the 7121F laminate is vapor breathable, and more vapor breathable than the 7327F sample for up to least 4 days of water contact. The results also show the 7121F laminate continues to be breathable beyond 4 days, which indicates laminate breathability can be maintained for time periods suitable for a variety of uses.

The results in Tables 3-5 also show significant effects of the varied fibre thickness from the mixed decitex fibre blend layer of the nonwoven fabric in laminate 7121F on hydrostatic head property when compared to that of the 7327 laminate, while the 7121F laminate provided hydrostatic head property which can be suitable for various laminate uses such as indicated herein. Air permeability results were not significantly different for the different tested laminates. The nonwoven fabric film composite of the 7121 F laminate is started with a normally non-breathable LDPE extruded onto the surface of the first decitex and second decitex fibre blend nonwoven fabric and having differential adhesion properties. While not desiring to be bound to a particular theory, upon extrusion lamination and cooling, it is believed that channels (viz., thinner film areas/zones along the polyester fibre) are created in the film through which unidirectional (one direction) air permeability is formed in the laminate. The laminate, such as illustrated by sample 7121F, also has a barrier property for bacteria penetration meeting EN 13795 Norm. The laminate also has the absorbency character available on one side. It is possible to extend to both sides if desired through the use of another nonwoven fabric. Air permeability also is possible from both sides. As also indicated by the results in Table 3, it was observed that the further application of a post-production calendering process to both laminates did not improve the function of air permeability and hydrostatic head, but deteriorated both properties. Lamination strength was observed to be greater for the 7327 F laminate, which is believed to be attributable to its relatively less profiled/rough fabric surface than the 7121 F laminate. Absorption was observed to be generally equivalent for both the 7327 F and 7121 F laminates.

Figure 5:
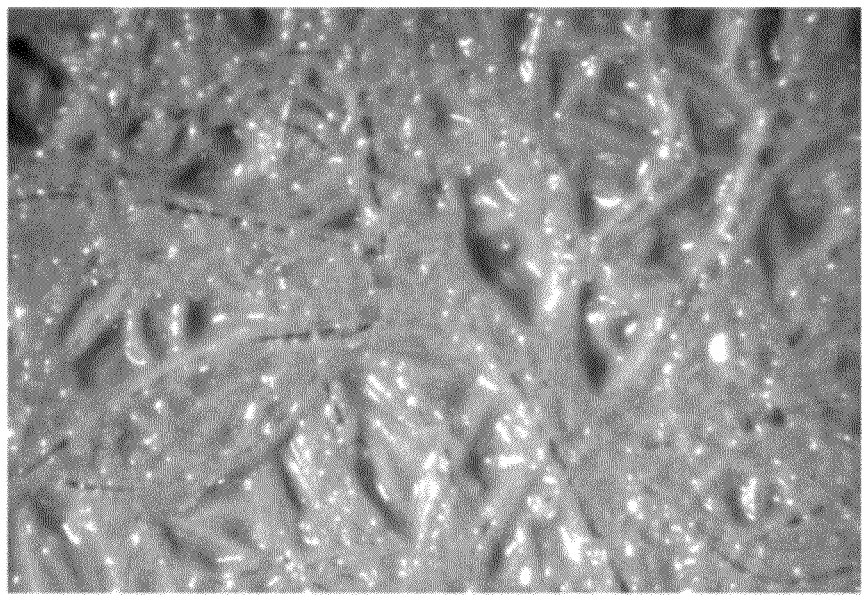
FIG. 5 is a microphotograph (200× magnification) from the non-laminated film side of a film of a breathable laminate in accordance with an embodiment of the present invention.
Figure 6:
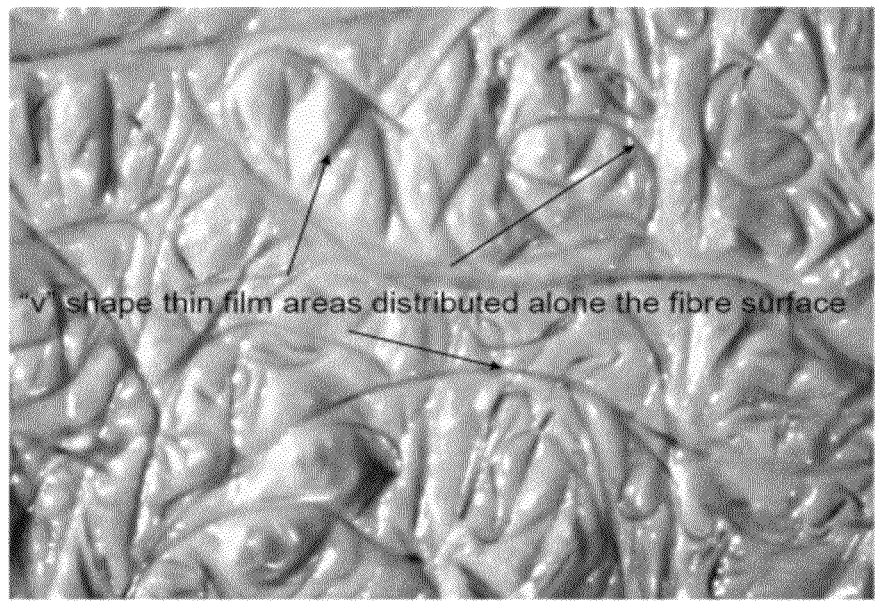
FIG. 6 is a microphotograph (200×) from a laminated film side of a film of a breathable laminate in accordance with an embodiment of the present invention.
Figure 7:
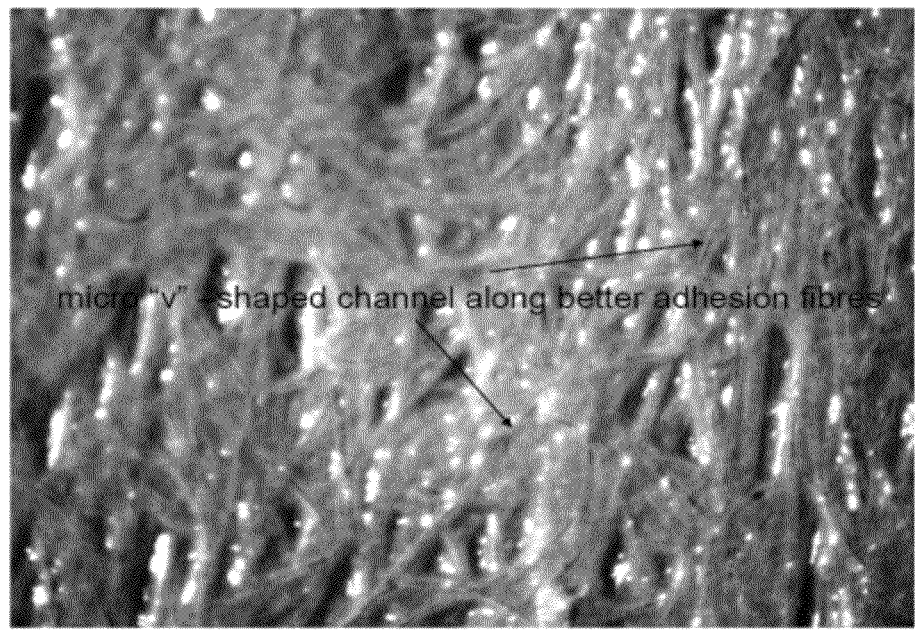
FIG. 7 is a microphotograph (200×) from the non-laminated film side of a film of a comparison laminate.
Figure 8:
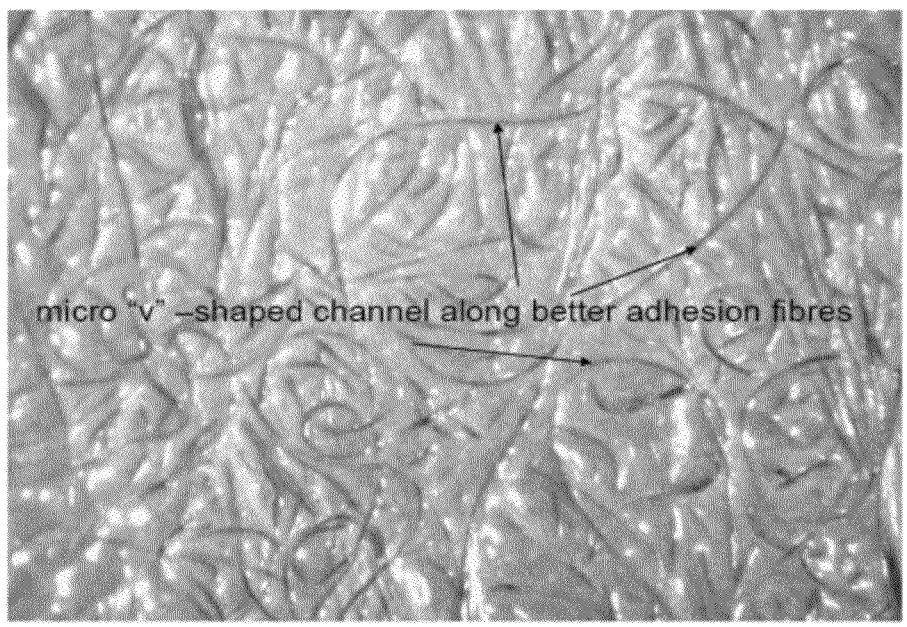
FIG. 8 is a microphotograph (200×) from the laminated film side of a film of a comparison laminate.
Figure 9:
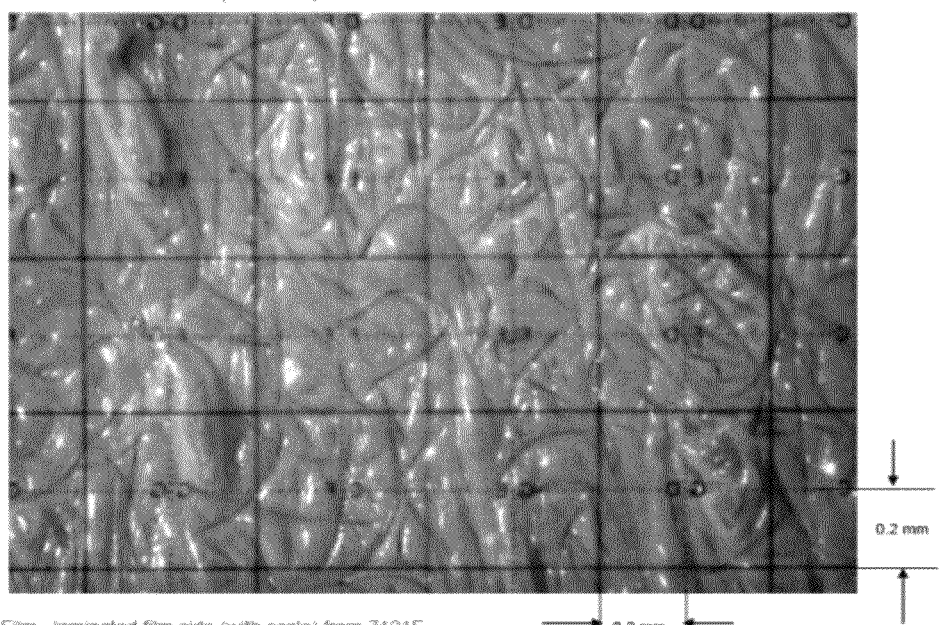
FIG. 9 is a microphotograph (200×) from the laminated film side, with scale, of a film of a comparison laminate.
Figure 10:
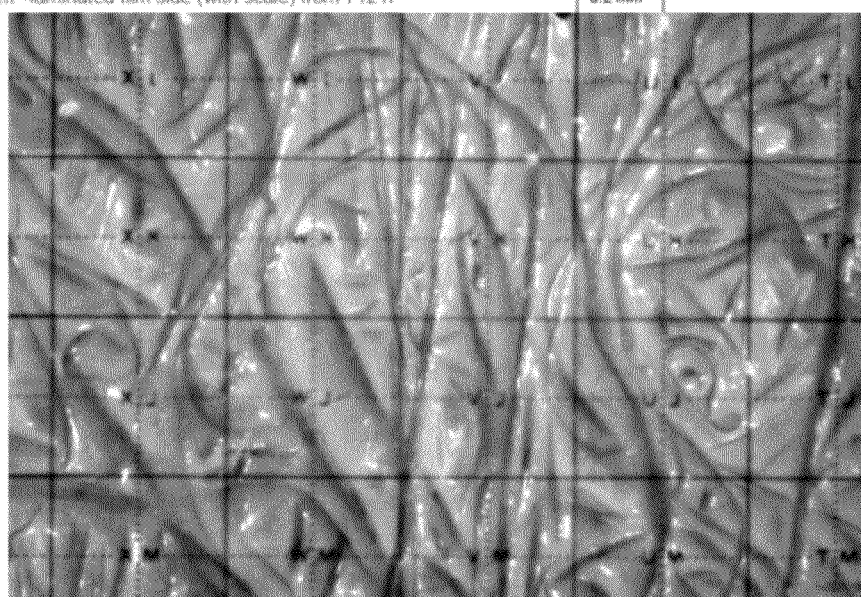
FIG. 10 is a microphotograph (200×) from the laminated film side, with scale, of a film of a breathable laminate in accordance with an embodiment of the present invention.

To further understand the film behavior after extrusion lamination, microscopic examination was carried out on film delaminated from the 7121 F laminate (i.e., nonwoven fabric sample 1 laminated with LDPE film) and the 7327 F laminate (i.e., nonwoven fabric sample A laminated with LDPE film). FIGS. 5 and 6 show an enlarged portion of the surface of the film from the non-laminated side (i.e., the side opposite to the nonwoven fabric) and the laminated side (i.e., side facing the nonwoven fabric) of the film of the 7121 F laminate. These microphotographs are taken by using DigiMicro Scale microscope with 200× magnification. This DigiMicro Scale microscope is made by Drahtlose Nachrichtentechnik Entwicklungs- und Vertriebs GmbH, Dietzenbach, Germany. FIGS. 7 and 8 show an enlarged portion of the surface of the film from the non-laminated side (i.e., the side opposite to the nonwoven fabric) and the laminated side (i.e., side facing the nonwoven fabric) of the film of the 7327 F laminate. FIGS. 9 and 10 show scaled photographs from the laminated film side of the 7327 F and 7121 F laminates, respectively.

FIGS. 11 and 12 show scaled photographs with thread markings indicated of the 7327 F and 7121 F laminates, respectively. These figures show microscale "V" shape channels in the film areas coinciding along locations of polyester fibres on the nonwoven fabric.

The lengths of the "V" thinned regions based on film surface area for the films of the 7121 F and 7327 F composites were determined. The fibre lengths on the film were marked as shown in FIGS. 11 and 12 as first measured by thread, and thread length is transferred to scaled graph paper (not shown). Calculations were performed knowing the total length and the scale, as follows.

Total length of thinned film region of 7121F (excluding the VA binder deposit)=(259+285)=544 units. Every 14 units=0.2 mm. Thus, 544 units=(544×0.2/14) mm=7.8 mm. That is, it has 7.8 mm V-shape thinned length per (4×0.2 mm)$^2$=7.8 mm/0.64 mm$^2$. Total length of thinned film region of 7121F (including the purposely implant thick VA binder deposit)=(259+285+32) units=576 units. Every 14 units=0.2 mm. Thus, 576 units=(576×0.2/14) mm=8.2 mm. That is, it has 8.2 mm v-shape thinned length per (4×0.2 mm)$^2$=8.2 mm/0.64 mm$^2$. Total length of thinned film region of 7327F (excluding the VA binder deposit)=(257+308)=565 units. Every 14 units=0.2 mm. Thus, 565 units=(565×0.2/14) mm=8.1 mm. That is, it has 8.1 mm v-shape thinned length per (4×0.2 mm)$^2$=8.1 mm/0.64 mm$^2$.

Figure 13:
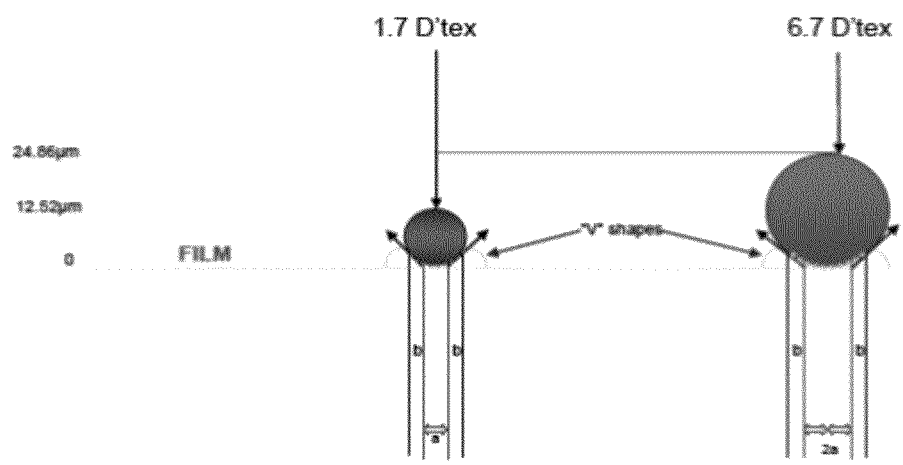
FIG. 13 is a schematic view of the interaction of first decitex (i.e., coarse) fibres and second decitex (i.e., fine) fibres of a nonwoven fabric with a backing film layer in accordance with an embodiment of the present invention.

FIG. 13 schematically illustrates the influence of the extruded film thickness (deformation to the film thickness) caused by the nonwoven fabric surface roughness due to the presence of the coarse polyester fibres with the finer viscose rayon fibres (i.e., 6.7 Dtex versus 1.7 Dtex). The cross sectional view as shown in FIG. 13 at regions "a" and "b" illustrate the thinner areas on the laminated film.

The area percentage of the "V" thinned regions based on film surface area for air permeability and hydrostatic head for the films of the 7121 F and 7327 F laminates were determined. Assuming the "b" region for 1.7 dtex<"b" region for 6.7 dtex, as illustrated in FIG. 13, the percentages of thinned regions in the film for air permeability and hydrostatic head were determined as follows:

For the 7327 F laminate, the potential thinned region for air permeability is estimated to be (Length=8.1 mm)×(2b=0.667)×(Ø of 1.7 dtex=0.0125 mm)=(0.0675 mm$^2$/0.64 mm$^2$)%=10.55%. The potential thinned region for Hydrostatic Head is estimated to be (Length=8.1 mm)×((2b+a)=1)×(Ø of 1.7 dtex=0.0125 mm)=(0.1013 mm$^2$/0.64 mm$^2$)%=15.82%.

For the 7121F laminate, the potential thinned region for air permeability is estimated to be (Length=8.1 mm)×(2b=0.5)×(Ø of 6.7 dtex=0.02486 mm)=(0.1007 mm$^2$/0.64 mm$^2$)%=15.73%. The potential thinned region for Hydrostatic Head is estimated to be (Length=7.8 mm)×((2b+a)=1)×(Ø of 6.7 dtex=0.02486 mm)=(0.2014 mm$^2$/0.64 mm$^2$)%=31.46%. From these calculations, a significantly increased amount of effective thinned regions associated with the use of the mixed decitex nonwoven fabric in the 7121 F laminate as compared to the single decitex nonwoven fabric of the 7327 F laminate were shown.

Although not desiring to be bound to any theory, it is thought that only the V-shape regions (b-areas as indicated in FIG. 13) are responsible for air leakage if fibres clinging to the film are not detached slightly from the film. This would explain why air can go in one direction only or to be measured in one direction only when air suction is created when the laminate with fibres is facing the suction side. If the film is facing the suction side, any thinned localized regions are blocked by fibres placed on the V-shape regions. Zero air permeability is measured.

The "V" shapes have thin regions along the polyester fibres which are thought to be responsible for air leakage when the fibrous nonwoven fabric matt tends to be detached from the film during the air permeability measurement procedure. Air porosity of approximately 2.5 l/m$^2$/s was detached under the air suction of 196 Pa/20 cm$^2$, using a TEXTEST FX3300 air permeability tester, TEXTEST AG, Zurich, Switzerland, for both nonwoven fabric composites. When the tests were conducted on the reverse side of the nonwoven fabric composite, there is no air permeability measured. The above-indicated theory is thought to explain why there was no significant apparent difference observed in air porosity (under the testing conditions used) between the 7121F and 7323F even though 7121F involves 6.7 dtex PET fibres. The b-regions stay the same with 1.7 dtex PET fibres as with 6.7 dtex fibres when the length stays the same for both fabrics. The same length for both fabrics is control through the amount of PET fibres used to engineer the fabric surfaces.

The hydrostatic head is an indication of barrier property or water resistance. It also is an indication of an equivalent pore size or equivalent thinned localized areas of the film layer. The dotted curves of FIG. 13 illustrate "7121F" with coarse polyester, i.e. 6.7 Dtex/38 mm, that has potentially more thinned localized areas than "7327F", especially under water pressure. As indicated, the "7121F" laminate was observed to have lower HSH as compared to the "7327F" laminate in the tests done. The "7121F" laminate also has higher WVTR as compared to the "7327F" laminate as measured by ISO 15106-3 −23° C./in contact with water.

Unless indicated otherwise, all amounts, percentages, ratios and the like used herein are by weight. When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

The invention claimed is:

1. A breathable laminate comprising a liquid-resistant, vapor-permeable backing film layer co-extensively in direct joined contact with a liquid- and vapor-permeable nonwoven fabric, wherein the backing film layer of the breathable laminate comprises thinned localized regions which are vapor-permeable and liquid-resistant and thicker regions which are vapor-impermeable and liquid-resistant, wherein the backing film layer comprises a thermoplastic resin-containing composition and the nonwoven fabric comprises a blend of first decitex fibres and second decitex fibres which differ by at least 1 decitex, wherein the first decitex fibres have a decitex in a range of from 3.5 to 15 and the second decitex fibres have a decitex in a range of from 0.5 to 3.5, and wherein the first decitex fibres are present in the blend in an amount of from 10% to 90% by weight and the second decitex fibres are present in the wherein the thinned localized regions comprise microscale V shape channels in the backing film layer, wherein the channels coincide along locations of the first decitex fibres on the nonwoven fabric.

2. The breathable laminate of claim 1, wherein a total surface area of the backing film layer is comprised of from 1% to 30% of the thinned localized regions and 99% to 70% of the thicker regions.

3. The breathable laminate of claim 1, wherein the backing film layer further forms a barrier to bacteria, viruses, and solid particulate matter.

4. The breathable laminate of claim 1 having a water vapor transmission rate (WVTR) of 8 g/m2/24 hours or greater as measured by ISO 15106-3.

5. The breathable laminate of claim 1 having an air porosity, as measured with film-side pressure or fabric-side suction, of at least 0.5 liters/m$^2$/s and an opposite side air porosity of less than 0.1 liters/m$^2$/s as measured by ENISO 9237.

6. The breathable laminate of claim 1 having a hydrostatic head of at least 5 or more at 10 mbar/min as measured with water pressure applied from an outer film side of the laminate as measured by EN 20811, and having a hydrostatic head of at least 5 or more at 10 mbar/min as measured with water pressure applied from a fabric side of the laminate as measured by EN 20811.

7. The breathable laminate of claim 1, wherein the thermoplastic resin of the backing film layer is low density polyethylene (LDPE), linear low density polyethylene (LLDPE), polypropylene (PP), ethylene vinyl acetate (EVA), ethylene methacrylate (EMA), or any coextrusion or blend thereof.

8. The breathable laminate of claim 1, wherein the first decitex fibres are polyester fibres and the second decitex fibres are viscose rayon fibres, and wherein the blend comprises from 55% to 75% by weight polyester fibres and from 45% to 25% by weight viscose rayon fibres.

9. The breathable laminate of claim 1, wherein the first decitex fibres have a decitex of from 5 to 8.5 and the second decitex fibres have a decitex of from 1 to 2.5.

10. The breathable laminate of claim 1, further comprising a binder selected from the group consisting of acrylic, ethylene vinyl acetate, vinyl-acrylic, styrene-butadiene rubber, and mixtures thereof.

11. The breathable laminate of claim 1, wherein the nonwoven fabric comprises a multilayered fibrous construction comprising a first nonwoven fabric layer directly adjacent the backing film layer and a second nonwoven fabric layer separated from the backing film layer by the first nonwoven fabric layer, wherein the first nonwoven fabric layer is the blend of first decitex fibres and second decitex fibres that differ by at least 1 decitex, and wherein the second nonwoven fabric layer is a second blend of fibres in a range of from 0.5 to 15 decitex wherein all the fibres in the second nonwoven fabric layer differ in decitex by less than 0.25 decitex.

12. The breathable laminate of claim 1, wherein the backing film layer has a basis weight of from 12 to 30 grams per square meter and a thickness of from 0.03 to 0.3 mm, and the nonwoven fabric has a basis weight of from 25 to 120 grams per square meter and a thickness of from 0.25 to 1.25 mm.

13. A disposable garment comprising the breathable laminate of claim 1.

14. A medical gown, medical drape, disposable diaper, sanitary napkin, panty liner, wound care article, wipe, or construction membrane, comprising the breathable laminate of claim 1.

15. A method of making a breathable laminate with varied vapor permeability, comprising steps of:
extruding a film comprising a thermoplastic resin-containing composition directly onto a liquid- and vapor-permeable nonwoven fabric to provide a film coated nonwoven fabric, wherein the nonwoven fabric comprises a blend of first and second decitex fibres which differ by at least 1 decitex, wherein the first decitex fibres have a decitex in a range of from 3.5 to 15 and the second decitex fibres have a decitex in a range of from 0.5 to 3.5, and wherein the first decitex fibres are present in the blend in an amount of from 10% to 90% by weight and the second decitex fibres are present in the blend in an amount of from 90% to 10% by weight; and
cooling the film coated nonwoven fabric to produce a liquid-resistant, varied vapor-permeable backing film layer co-extensively joined in direct contact with a liquid- and vapor-permeable nonwoven fabric, wherein the backing film layer comprises vapor-permeable, liquid-resistant thinned localized regions and vapor-impermeable and liquid-resistant thicker regions that remain after cooling the coated fabric, wherein the thinned localized regions comprise microscale V shape channels in the backing film layer, wherein the channels coincide along locations of first decitex fibres on the nonwoven fabric.

16. A breathable laminate comprising a liquid-resistant, vapor-permeable backing film layer co-extensively in direct joined contact with a liquid- and vapor-permeable nonwoven fabric, wherein the backing film layer of the breathable laminate comprises thinned localized regions which are vapor-permeable and liquid-resistant and thicker regions which are vapor-impermeable and liquid-resistant, wherein the backing film layer comprises a thermoplastic resin-containing composition and the nonwoven fabric comprises a blend of first decitex fibres and second decitex fibres which differ by at least 1 decitex, wherein the first decitex fibres comprise polyester fibres and have a decitex in a range of from 3.5 to 15 and the second decitex fibres have a decitex in a range of from 0.5 to 3.5, and wherein the first decitex fibres are present in the blend in an amount of from 10% to 90% by weight and the second decitex fibres are present in the blend in an amount of from 90% to 10% by weight, wherein the thinned localized regions comprise microscale V shape channels in the backing film layer, wherein the channels coincide along locations of the polyester fibres on the nonwoven fabric.

17. The breathable laminate of claim 16, wherein a total surface area of the backing film layer is comprised of from 1% to 30% of the thinned localized regions and 99% to 70% of the thicker regions.

18. The breathable laminate of claim 16, wherein the second decitex fibres are viscose rayon fibres, and wherein the blend comprises from 55% to 75% by weight polyester fibres and from 45% to 25% by weight viscose rayon fibres.

19. The breathable laminate of claim 1, wherein the breathable laminate permits passage of air flow from one direction only across the breathable laminate.

20. The breathable laminate of claim 1, wherein the thinned localized regions have a solid film composition of greater than 98% by volume and the thicker regions have another solid film composition of greater than 99% by volume.

* * * * *